(12) United States Patent
Lee et al.

(10) Patent No.: US 11,242,357 B2
(45) Date of Patent: *Feb. 8, 2022

(54) FUSED POLYCYCLIC HETEROAROMATIC COMPOUND AND ORGANIC THIN FILM AND ELECTRONIC DEVICE

(71) Applicant: Samsung Electronics Co., Ltd., Suwon-si (KR)

(72) Inventors: Don-Wook Lee, Seoul (KR); Jeong Il Park, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 79 days.

This patent is subject to a terminal disclaimer.

(21) Appl. No.: 16/140,661

(22) Filed: Sep. 25, 2018

(65) Prior Publication Data

US 2019/0112319 A1    Apr. 18, 2019

(30) Foreign Application Priority Data

Oct. 18, 2017    (KR) ........................ 10-2017-0135397

(51) Int. Cl.
| | | |
|---|---|---|
| *C07D 517/22* | (2006.01) | |
| *C07D 495/22* | (2006.01) | |
| *H01L 51/00* | (2006.01) | |
| *H01L 51/05* | (2006.01) | |

(52) U.S. Cl.
CPC ......... *C07D 517/22* (2013.01); *C07D 495/22* (2013.01); *H01L 51/0062* (2013.01); *H01L 51/0067* (2013.01); *H01L 51/0068* (2013.01); *H01L 51/0071* (2013.01); *H01L 51/0072* (2013.01); *H01L 51/0074* (2013.01); *H01L 51/0541* (2013.01); *H01L 51/0545* (2013.01); *H01L 51/0558* (2013.01)

(58) Field of Classification Search
CPC . C07D 517/22; C07D 495/22; H01L 51/0071; H01L 51/0068; H01L 51/0062; H01L 51/0072; H01L 51/0067; H01L 51/0074; H01L 51/0541; H01L 51/0545; H01L 51/0558; Y02E 10/549
USPC ...................................... 252/500, 75; 549/41
See application file for complete search history.

(56) References Cited

U.S. PATENT DOCUMENTS

| | | | |
|---|---|---|---|
| 5,946,551 A | 8/1999 | Dimitrakopoulos et al. | |
| 6,232,157 B1 | 5/2001 | Dodabalapur et al. | |
| 7,816,673 B2 | 10/2010 | Park et al. | |
| 8,124,964 B2 | 2/2012 | Takimiya et al. | |
| 8,138,355 B2 | 3/2012 | Watanabe | |
| 8,211,619 B2 | 7/2012 | Morita et al. | |
| 8,232,546 B2 | 7/2012 | Takimiya et al. | |
| 8,367,717 B2 | 2/2013 | Kastler et al. | |
| 8,658,805 B2 | 2/2014 | Park et al. | |
| 8,828,642 B2 | 9/2014 | Kamogawa et al. | |
| 9,018,630 B2 | 4/2015 | Takimiya et al. | |
| 9,096,621 B2 | 8/2015 | Hoffmann et al. | |
| 9,373,795 B2 | 6/2016 | Burroughes et al. | |
| 9,431,619 B2 | 8/2016 | Lee et al. | |
| 9,537,102 B2 | 1/2017 | Park et al. | |
| 9,853,225 B2 | 12/2017 | Takeya et al. | |
| 9,988,472 B2 | 6/2018 | Lee et al. | |
| 10,056,563 B2 | 8/2018 | Miyazaki et al. | |
| 10,651,255 B2* | 5/2020 | Choi ................... | H01L 51/0545 |
| 10,686,145 B2* | 6/2020 | Lee ......................... | C09B 57/00 |
| 11,069,863 B2* | 7/2021 | Kuzumoto ........... | C07D 517/04 |
| 2008/0142792 A1 | 6/2008 | Park et al. | |
| 2010/0065826 A1 | 3/2010 | Takimiya et al. | |
| 2011/0224445 A1 | 9/2011 | Takimiya | |
| 2013/0116447 A1* | 5/2013 | Park ..................... | C07D 495/22 |
| | | | 549/41 |
| 2013/0277657 A1* | 10/2013 | Park ..................... | C07D 495/22 |
| | | | 257/40 |
| 2013/0320316 A1* | 12/2013 | Park .................... | H01L 51/0074 |
| | | | 257/40 |
| 2015/0133679 A1 | 5/2015 | Park et al. | |
| 2016/0226005 A1 | 8/2016 | Park et al. | |
| 2017/0069854 A1* | 3/2017 | Lee .................... | H01L 51/0074 |
| 2019/0036037 A1 | 1/2019 | Lee et al. | |
| 2020/0168806 A1* | 5/2020 | Lee ......................... | H01L 51/05 |
| 2020/0176690 A1* | 6/2020 | Kuzumoto .......... | C07D 495/22 |

FOREIGN PATENT DOCUMENTS

| | | |
|---|---|---|
| EP | 1932847 A1 | 6/2008 |
| EP | 3125321 A1 | 2/2017 |
| EP | 3301207 A1 | 4/2018 |
| EP | 3522243 A1 | 8/2019 |
| JP | 2007-122029 A | 5/2007 |
| JP | 2009-267134 A | 11/2009 |
| JP | 2010018529 A * | 1/2010 |
| JP | 2010-150229 A | 7/2010 |
| JP | 2010-177643 A | 8/2010 |
| JP | 2010-254599 A | 11/2010 |
| JP | 2011-526588 A | 10/2011 |
| JP | 4958119 B2 | 6/2012 |
| JP | 2015-170758 A | 9/2015 |
| JP | 2015-192116 A | 11/2015 |
| KR | 20080054553 A | 6/2008 |
| KR | 2013-0050266 A | 5/2013 |
| KR | 2013-0136938 A | 12/2013 |

(Continued)

OTHER PUBLICATIONS

English translation of JP 2010-177643, Aug. 12, 2010. (Year: 2010).*

(Continued)

*Primary Examiner* — Douglas J McGinty
(74) *Attorney, Agent, or Firm* — Harness, Dickey & Pierce, P.L.C.

(57) ABSTRACT

A fused polycyclic heteroaromatic compound represented by Chemical Formula 1, and an organic thin film, an organic thin film transistor, and an electronic device including the fused polycyclic heteroaromatic compound are provided. The fused polycyclic heteroaromatic compound may have a conjugation structure but reinforce planarity among adjacent rings and have further dense packing and thus much increase charge mobility.

16 Claims, 4 Drawing Sheets

(56) References Cited

FOREIGN PATENT DOCUMENTS

| KR | 10-2014-0041439 A | 4/2014 |
| KR | 10-2014-0064965 A | 5/2014 |
| KR | 2016-0093550 A | 8/2016 |
| KR | 10-2019-0013429 A | 2/2019 |
| WO | WO-08-026602 A1 | 3/2008 |
| WO | WO-2009/0009790 A1 | 1/2009 |
| WO | WO-2012-118174 A1 | 9/2012 |
| WO | WO-14-136827 A1 | 9/2014 |
| WO | WO-2016-117389 A1 | 7/2016 |
| WO | WO-2016-148170 A1 | 9/2016 |
| WO | WO-2018-061821 A1 | 4/2018 |

OTHER PUBLICATIONS

STN CAS reg. No. 2306280-69-1, May 7, 2019. (Year: 2019).*
Claims for U.S. Appl. No. 16/661,631, allowed as U.S. Pat. No. 11,069,863, 14 pages. (Year: 2021).*
Fei, Zhuping et al. Influence of Backbone Fluorination in Regioregular Poly (3-alkyl-4-fluoro) thiophenes. J. Am. Chem. Soc. 2015, 137, 6866-6879.
Nakayama, Kengo, et al., "Patternable Solution—Crystallized Organic Transistors with High Charge Carrier Mobility" Advanced Materials, 2011, 23, 1626-1629.
He, Keqiang, et al., "Asymmetric Conjugated Molecules Based on [1]Benzothieno[3,2-b][1]benzothiophene for High-Mobility Organic Thin-Film Transistors: Influence of Alkyl Chain Length," ACS Applied Materials & Interfaces, Sep. 26, 2017.
Extended European Search Report dated May 7, 2020, issued in corresponding European Patent Application No. 19204586.2.
Non-Final Office Action dated Nov. 18, 2020 in U.S. Appl. No. 16/661,631.
STN Search Conducted Nov. 12, 2020.
Final Office Action dated Jan. 19, 2021 in U.S. Appl. No. 16/661,631.
Notice of Allowance dated Mar. 19, 2021 in U.S. Appl. No. 16/661,631.

* cited by examiner

FUSED POLYCYCLIC HETEROAROMATIC COMPOUND AND ORGANIC THIN FILM AND ELECTRONIC DEVICE

CROSS-REFERENCE TO RELATED APPLICATION

This application claims priority to Korean Patent Application No. 10-2017-0135397, filed in the Korean Intellectual Property Office on Oct. 18, 2017, and all the benefits accruing therefrom under 35 U.S.C. § 119, the entire contents of which are incorporated herein by reference.

BACKGROUND

1. Field

Example embodiments relate to a fused polycyclic heteroaromatic compound, an organic thin film, and an electronic device.

2. Description of the Related Art

Flat panel display devices, e.g., liquid crystal display devices or organic electro-luminescence display devices, are provided with a variety of thin film transistors (TFTs) to drive them. The thin film transistor may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, as an organic semiconductor material for a channel of the thin film transistor, organic materials, e.g., pentacene or polythiophene, have been studied. In the case of polymer or oligomer organic materials, e.g., F8T2 (poly(9,9-dioctylfluorene-co-bithiophene)) as a polythiophene-based material, a solution process, e.g., spin casting, may be desirably applied. However, problems of decreased charge mobility and increased off-state leakage current may be caused. Further, low-molecular-weight organic materials, e.g., pentacene, may have higher charge mobility of about 3.2 to about 5.0 cm²/Vs or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

Therefore, recently, the development of an organic semiconductor material, satisfying improved processibility as well as higher charge mobility may still be required.

SUMMARY

An embodiment provides a fused polycyclic heteroaromatic compound that may be applicable to an electronic device such as an organic thin film transistor.

Another embodiment provides an organic thin film including the fused polycyclic heteroaromatic compound.

Yet another embodiment provides an electronic device including the organic thin film.

According to an embodiment, a fused polycyclic heteroaromatic compound represented by Chemical Formula 1 is provided.

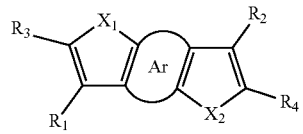

[Chemical Formula 1]

In Chemical Formula 1, $X_1$ and $X_2$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, Ar is a substituted or unsubstituted C6 to C30 aromatic ring, a substituted or unsubstituted C3 to C30 heteroaromatic ring, or a fused ring including the fused two or more rings, Ar is combined with an $X_1$-containing hetero ring and an $X_2$-containing hetero ring to provide a condensed polycyclic ring, $R_1$ and $R_2$ are independently hydrogen or a halogen atom, and $R_3$ and $R_4$ are independently a heterocyclic group including a heteroatom selected from N, S, Se, and Te, wherein the heteroatom is adjacent to carbon linked with the condensed polycyclic ring.

$R_3$ and $R_4$ of Chemical Formula 1 may independently be one of heterocyclic groups represented by Chemical Formula 2-1 and Chemical Formula 2-2.

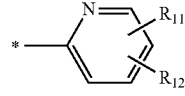

[Chemical Formula 2-1]

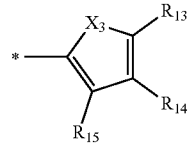

[Chemical Formula 2-2]

In Chemical Formula 2-1 and Chemical Formula 2-2, $X_3$ is S, Se, or Te, $R_{11}$ to $R_{14}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{15}$ is hydrogen or a halogen atom, $R_{11}$ and $R_{12}$ are independently present alone or combined to provide a ring, $R_{13}$ and $R_{14}$ are independently present alone or adjacent two thereof are combined to provide a ring, and * is a linking point with the condensed polycyclic ring of Chemical Formula 1.

The condensed polycyclic ring and the heterocyclic group represented by Chemical Formula 2-1 or Chemical Formula 2-2 may substantially be present in the same plane.

$R_{11}$ to $R_{15}$ may independently be hydrogen.

At least one of $R_1$ and $R_2$ may be a halogen atom.

$R_{15}$ may be a halogen atom and at least one of $R_1$ and $R_2$ may be a halogen atom.

The Ar may have four to eight rings.

The condensed polycyclic ring may be represented by one of Chemical Formula 3-1 to Chemical Formula 3-16.

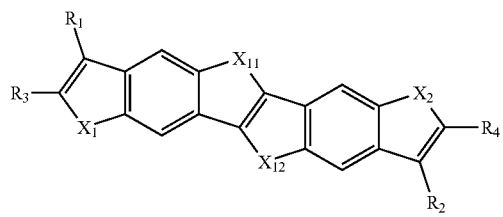

(3-1)

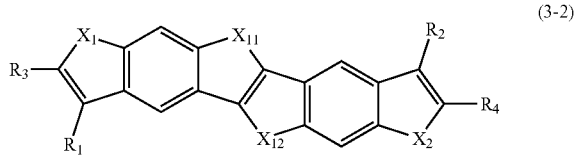

(3-2)

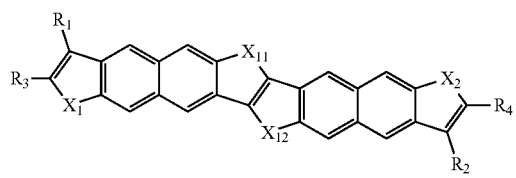

(3-3)

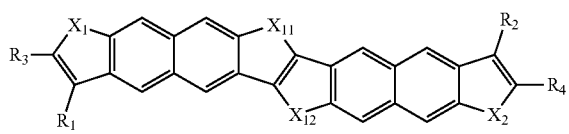

(3-4)

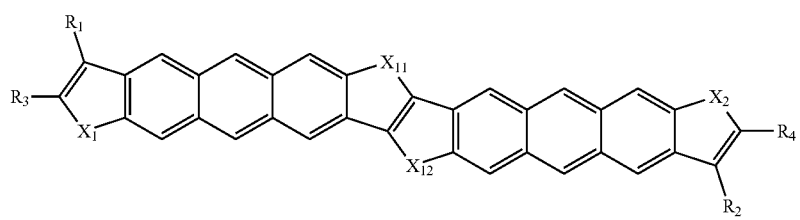

(3-5)

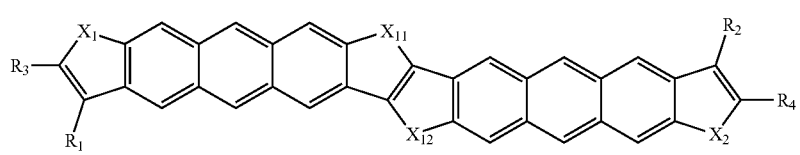

(3-6)

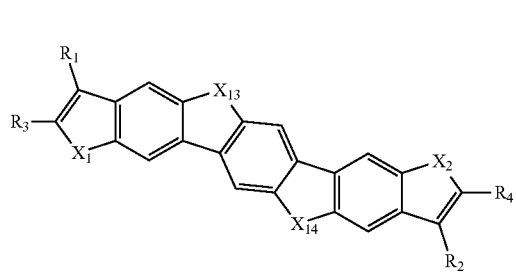

(3-7)

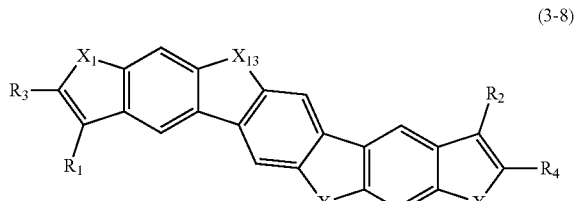

(3-8)

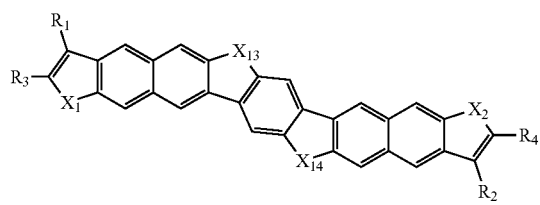

(3-9)

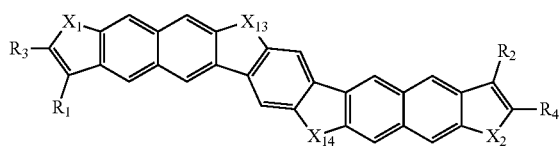

(3-10)

(3-11)
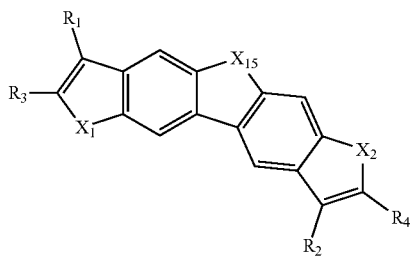

(3-12)
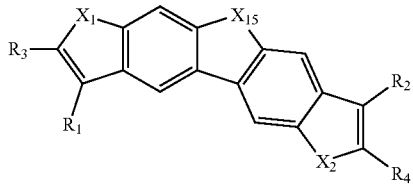

(3-13)
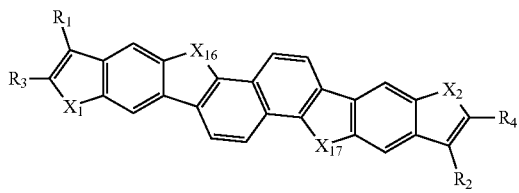

(3-14)
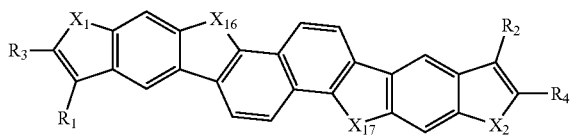

(3-15)
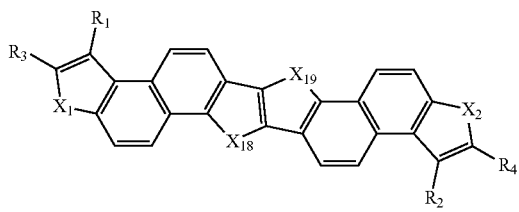

(3-16)
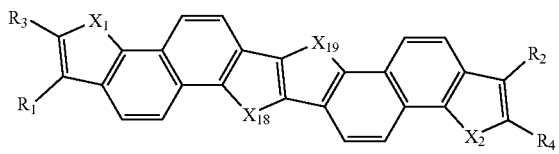

In Chemical Formula 3-1 to Chemical Formula 3-16, $X_1$, $X_2$, $R_1$, $R_2$, $R_3$, and $R_4$ are the same as in Chemical Formula 1, $X_{11}$ to $X_{19}$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof.

$R_3$ and $R_4$ may have the same heterocyclic groups.

The fused polycyclic heteroaromatic compound may be represented by Chemical Formula 4.

[Chemical Formula 4]

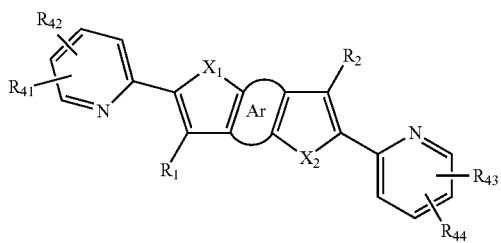

In Chemical Formula 4, $X_1$, $X_2$, Ar, $R_1$, and $R_2$ are the same as in Chemical Formula 1, $R_{41}$ to $R_{44}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{41}$ and $R_{42}$ are independently present alone or adjacent two thereof are combined to provide a ring, and $R_{43}$ and $R_{44}$ are independently present alone or adjacent two thereof are combined to provide a ring.

The fused polycyclic heteroaromatic compound may be represented by one of Chemical Formula 5-1 to Chemical Formula 5-36.

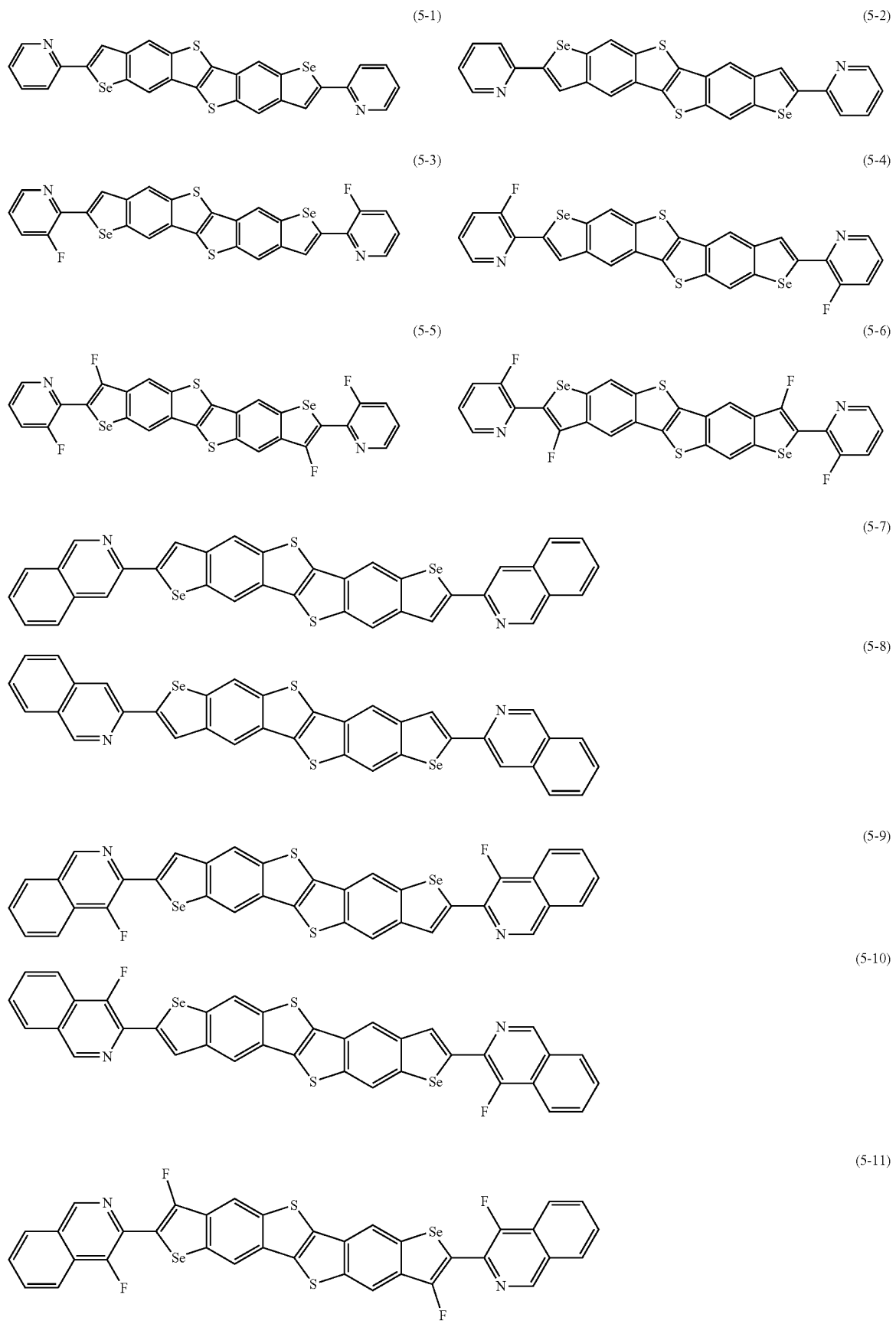

-continued
(5-12)
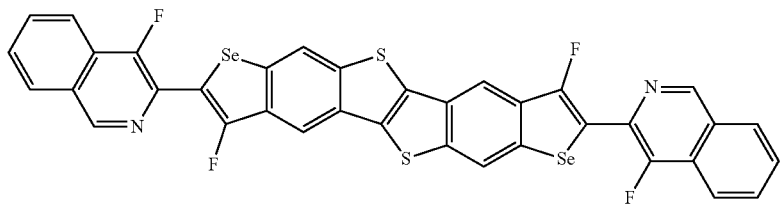
(5-13)
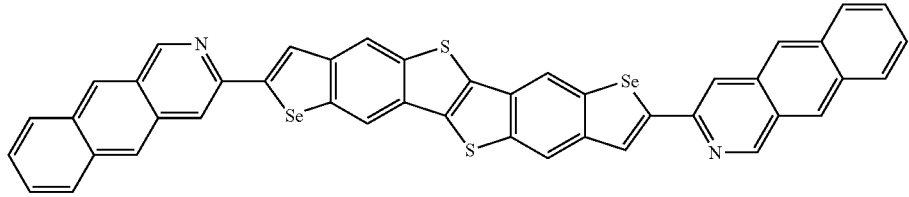
(5-14)
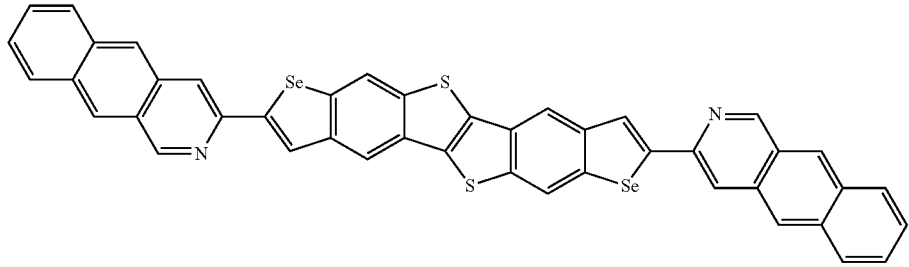
(5-15)
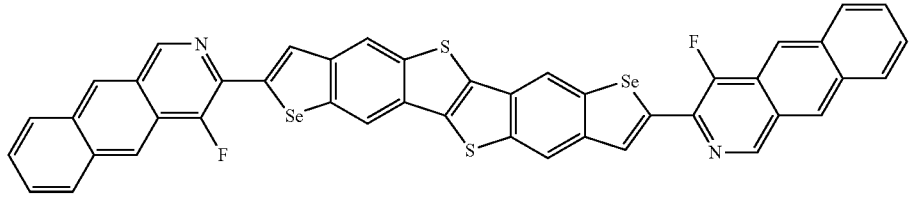
(5-16)
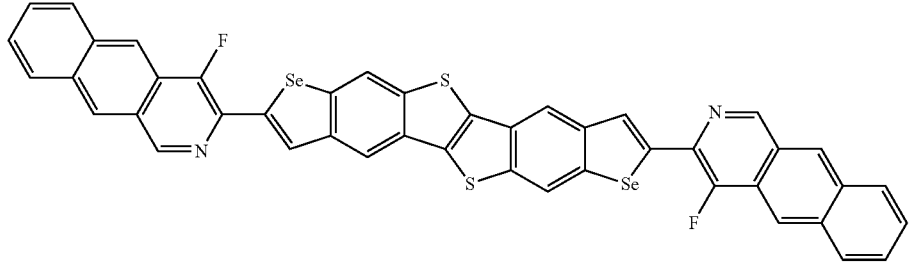
(5-17)
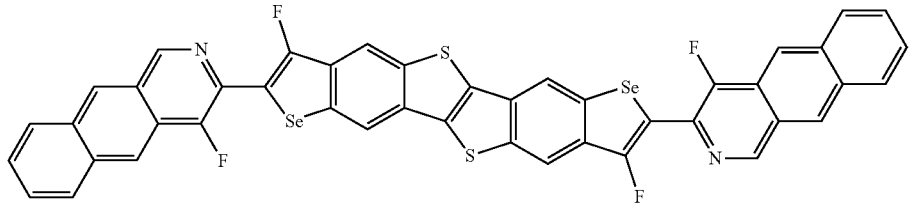

-continued
(5-18)
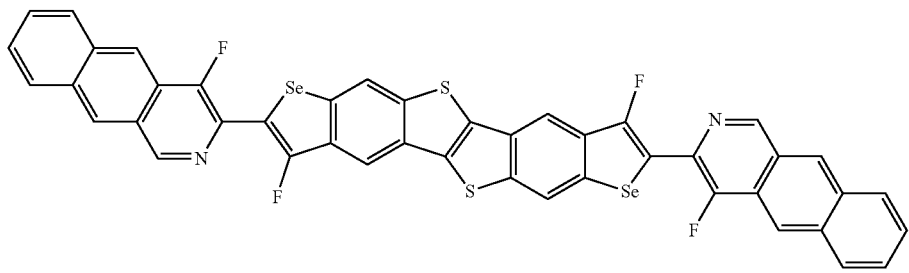
(5-19)
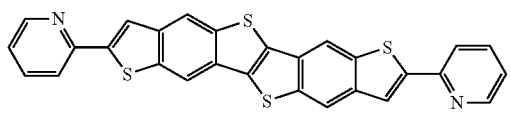
(5-20)
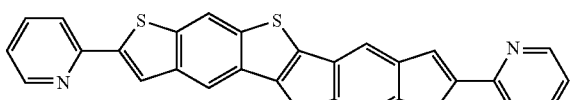
(5-21)
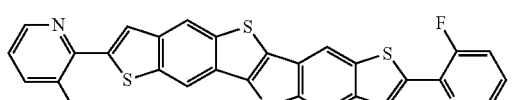
(5-22)
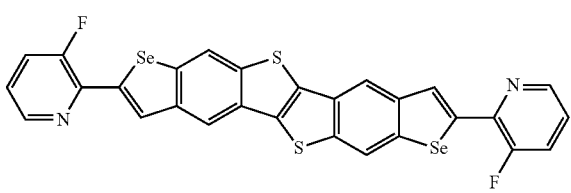
(5-23)
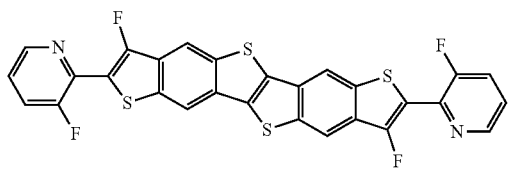
(5-24)
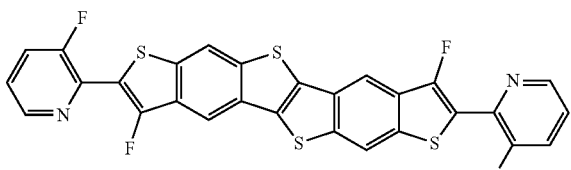
(5-25)
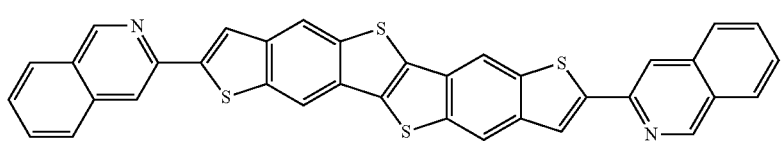
(5-26)
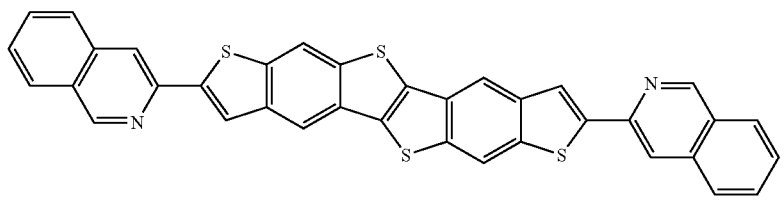
(5-27)
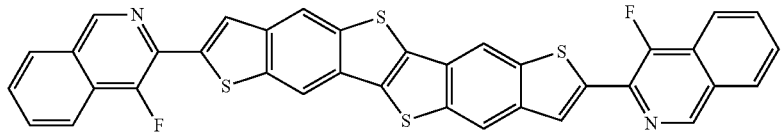
(5-28)
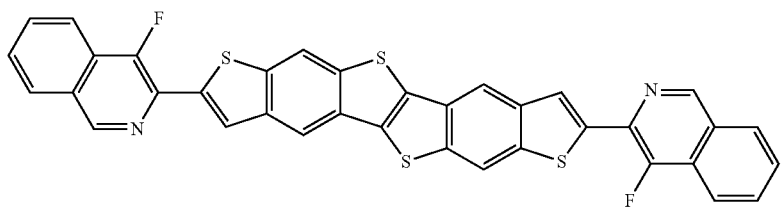

-continued
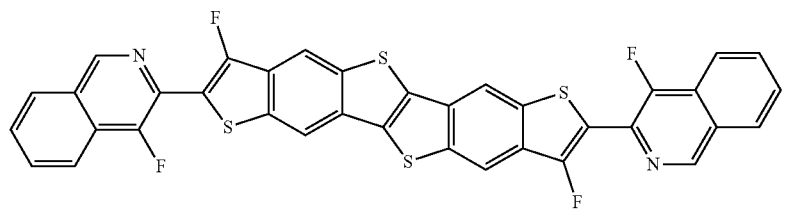
(5-29)
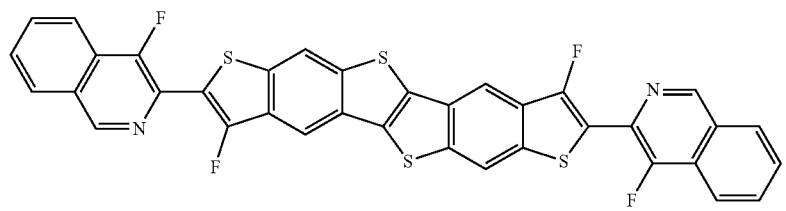
(5-30)
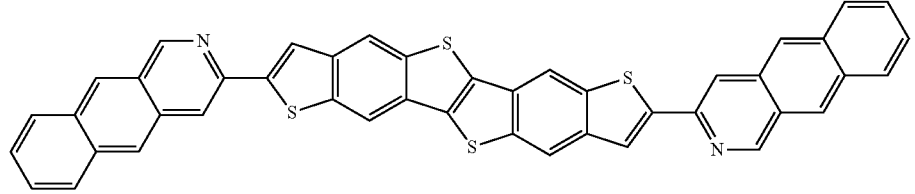
(5-31)
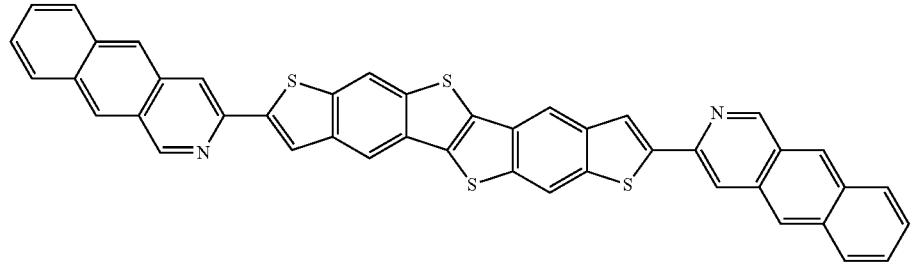
(5-32)
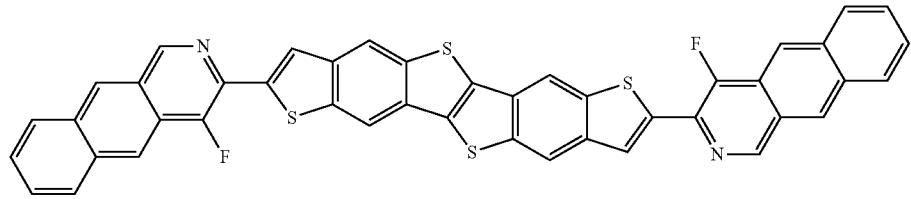
(5-33)
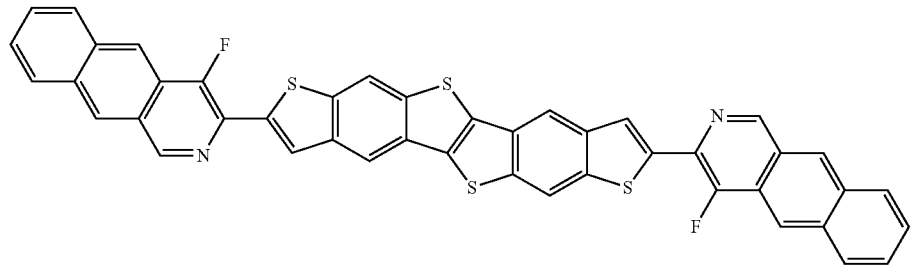
(5-34)
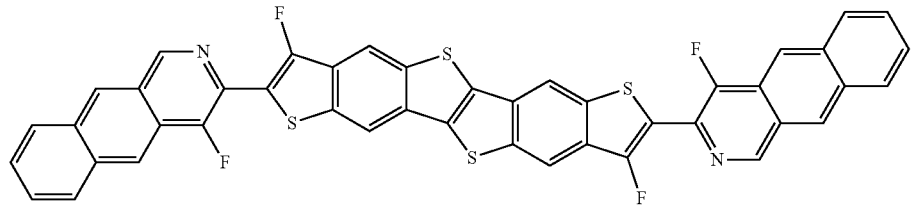
(5-35)

(5-36)

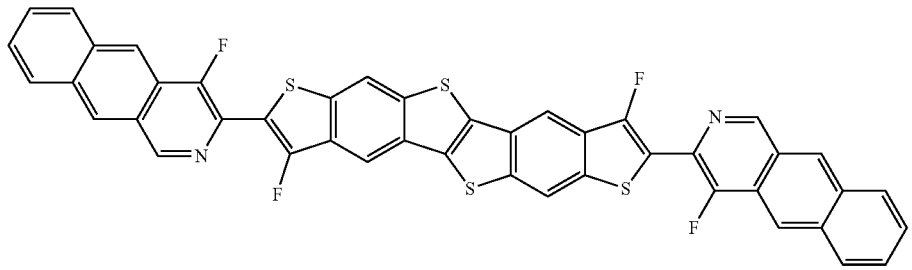

The fused polycyclic heteroaromatic compound may be represented by Chemical Formula 6.

[Chemical Formula 6]

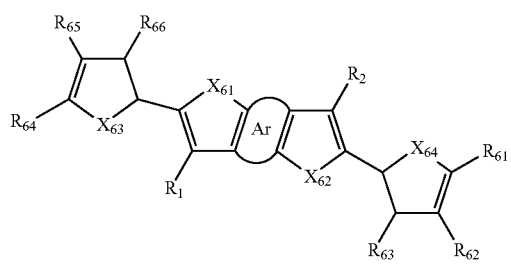

In Chemical Formula 6, Ar, $R_1$, and $R_2$ are the same as in Chemical Formula 1, $X_{61}$ to $X_{64}$ are independently S or Se, $R_{61}$, $R_{62}$, $R_{64}$, and $R_{65}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{63}$ and $R_{66}$ are independently hydrogen or a halogen atom, $R_{61}$ and $R_{62}$ are independently present alone or combined to provide a ring, and $R_{64}$ and $R_{65}$ are independently present alone or combined to provide a ring.

The fused polycyclic heteroaromatic compound may be represented by one of Chemical Formula 7-1 to Chemical Formula 7-24.

(7-1)

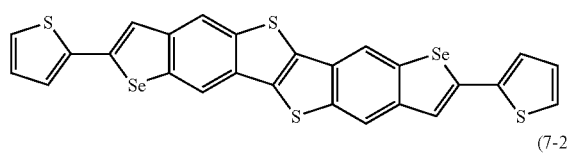

(7-2)

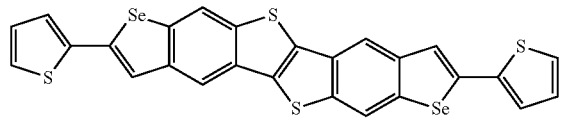

(7-3)

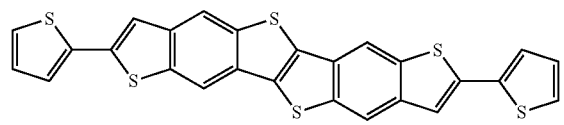

(7-4)

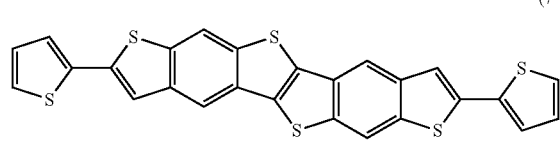

(7-5)

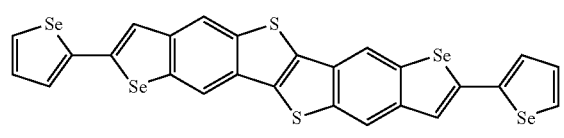

(7-6)

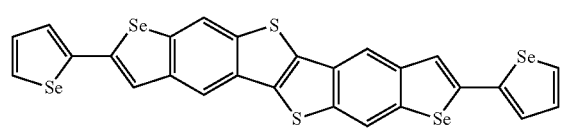

(7-7)

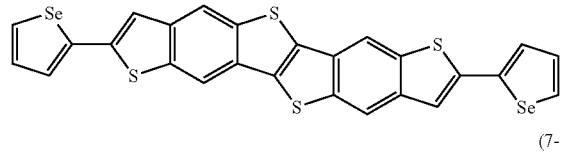

(7-8)

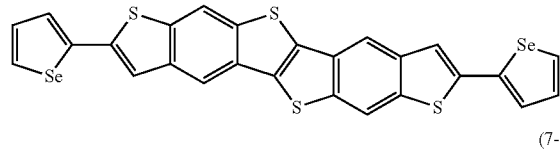

(7-9)

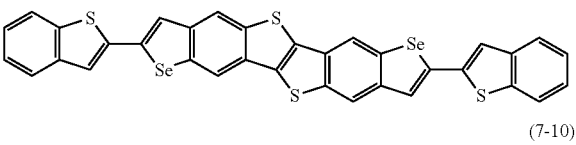

(7-10)

(7-11)
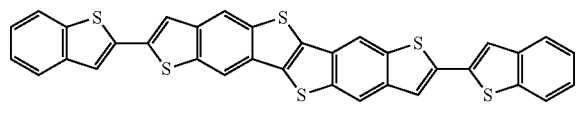
(7-12)
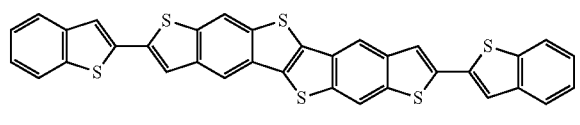
(7-13)
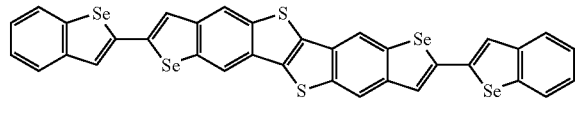
(7-14)
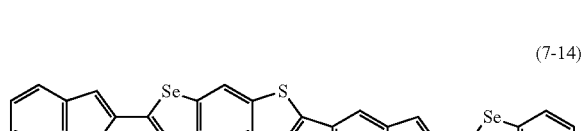
(7-15)
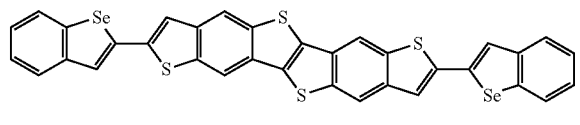
(7-16)
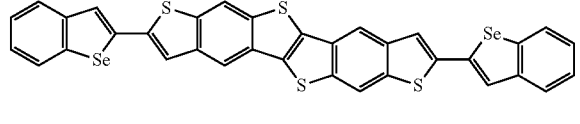
(7-17)
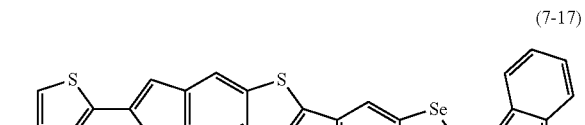
(7-18)
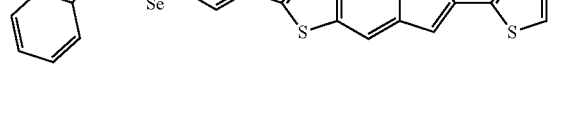
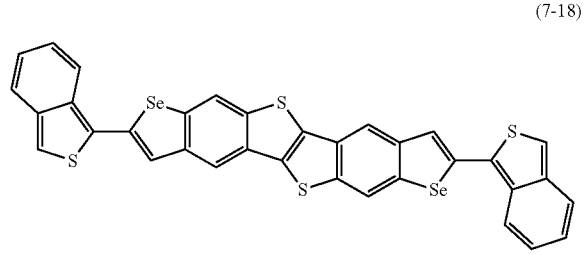
(7-19)
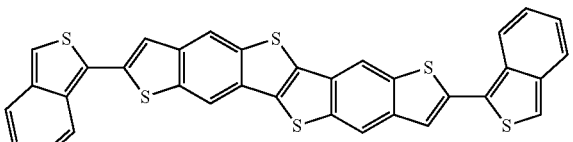
(7-20)
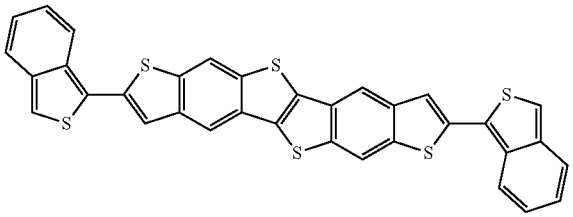
(7-21)
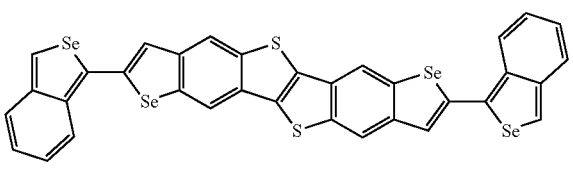
(7-22)
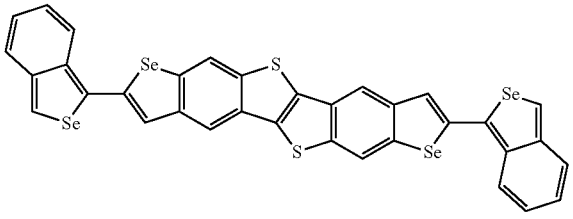
(7-23)
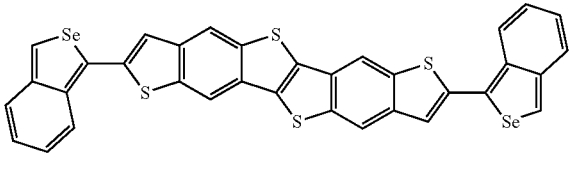
(7-24)
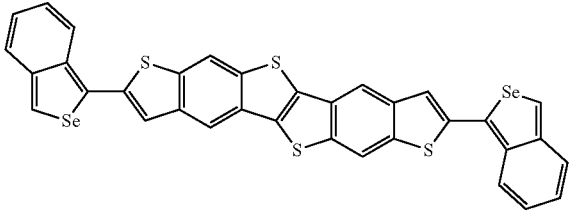
The fused polycyclic heteroaromatic compound may be represented by one of Chemical Formula 8-1 to Chemical Formula 8-20.

(8-1)
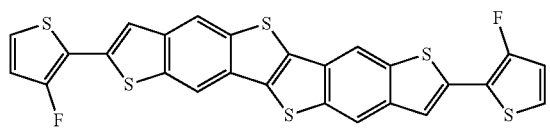
(8-2)
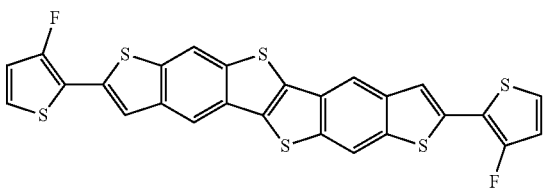
(8-3)
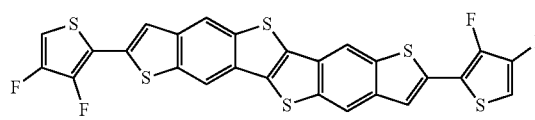
(8-4)
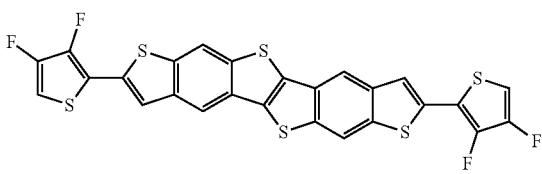
(8-5)
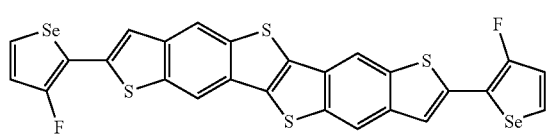
(8-6)
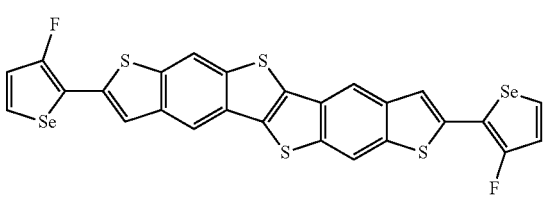
(8-7)
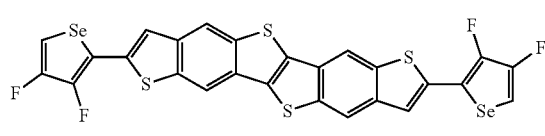
(8-8)
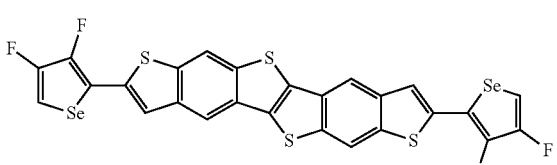
(8-9)
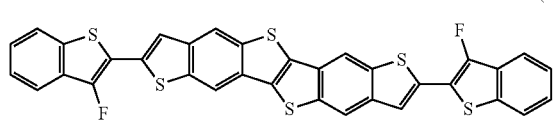
(8-10)
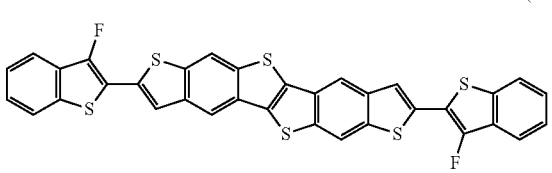
(8-11)
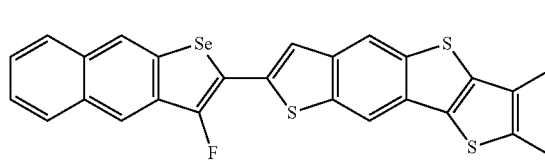
(8-12)
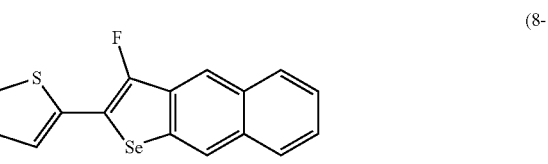
(8-13)
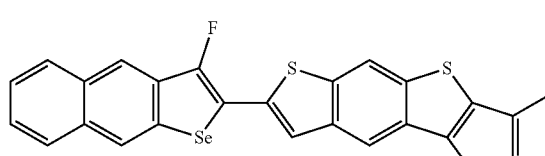
(8-14)
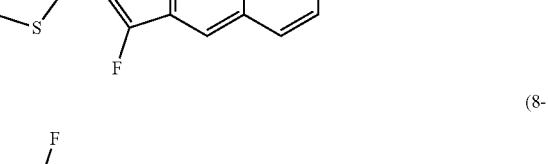
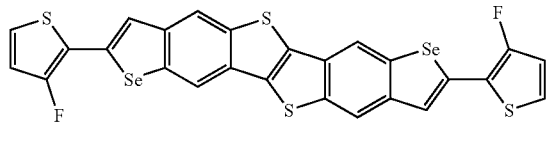
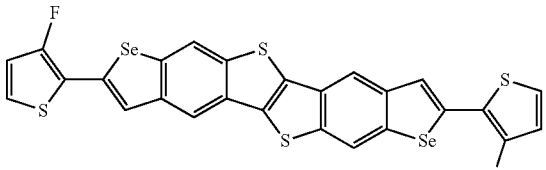

-continued
(8-15)
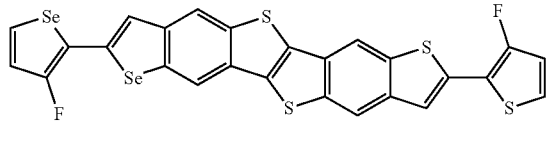
(8-16)
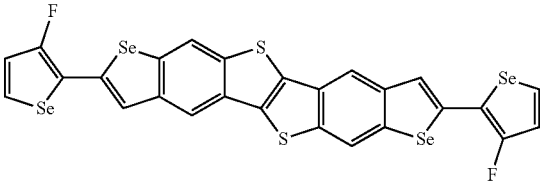
(8-17)
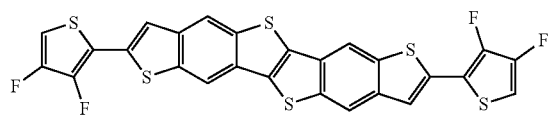
(8-18)
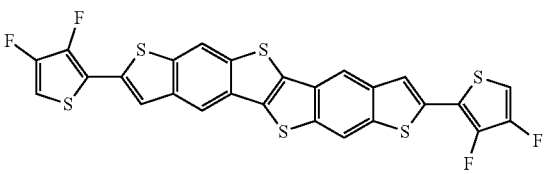
(8-19)
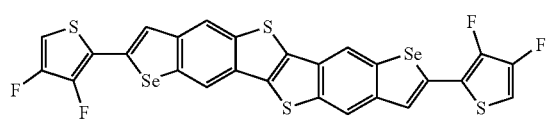
(8-20)
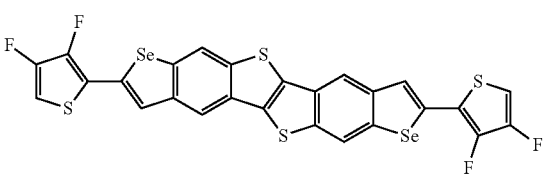
The fused polycyclic heteroaromatic compound may be represented by one of Chemical Formula 9-1 to Chemical Formula 9-42.
(9-1)
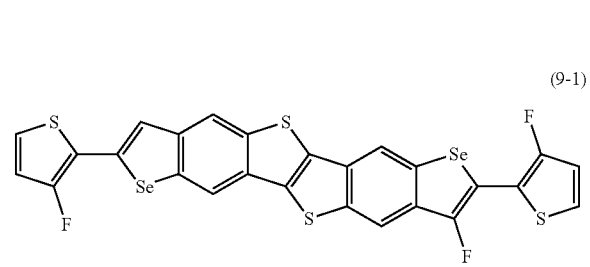
(9-2)
(9-3)
-continued
(9-4)
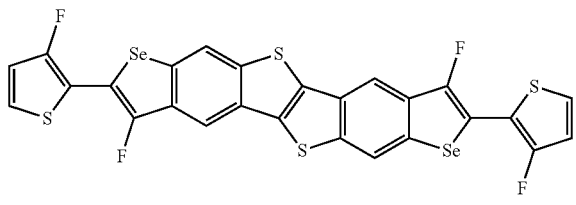
(9-5)
(9-6)
(9-7)
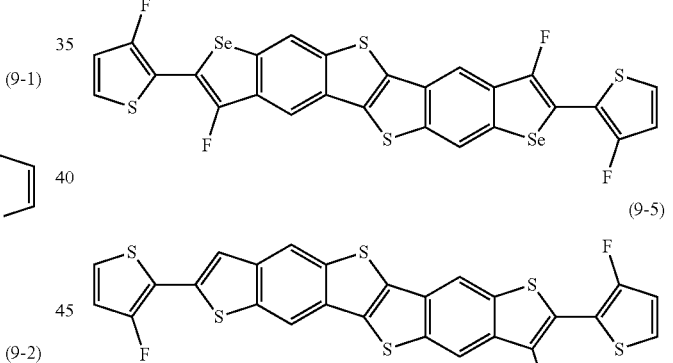
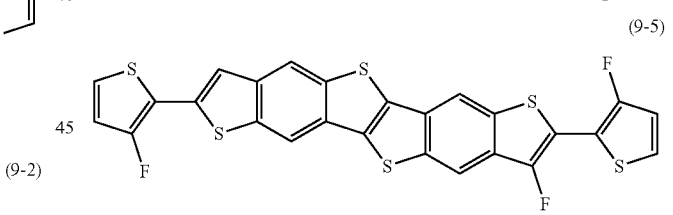
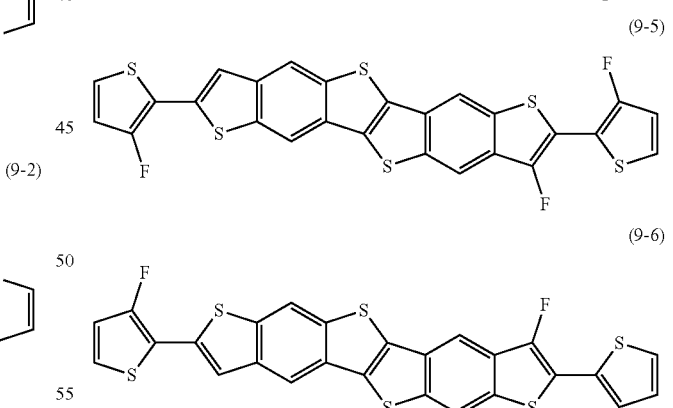
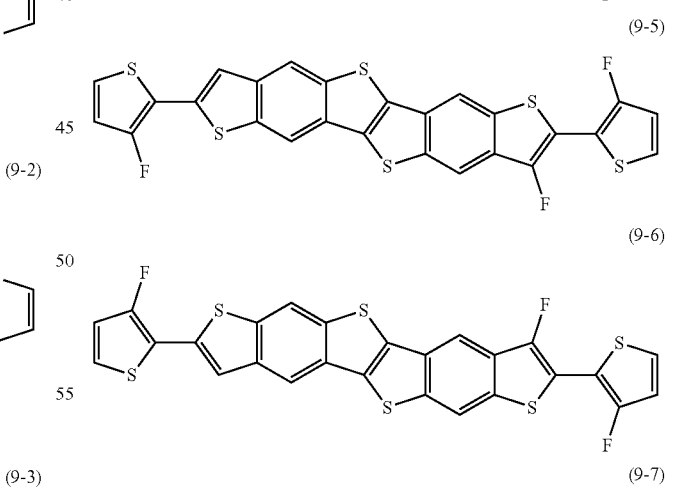
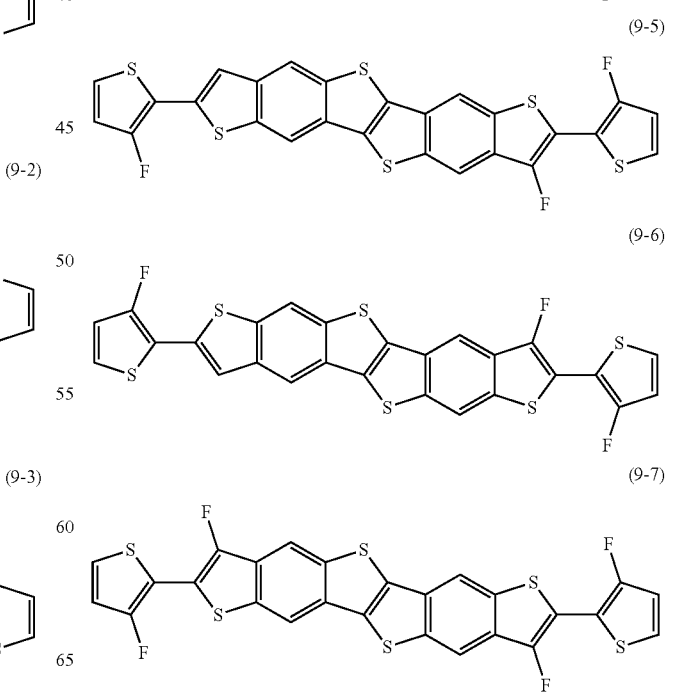

-continued
(9-8)
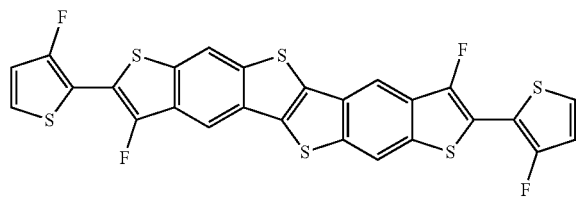
(9-9)
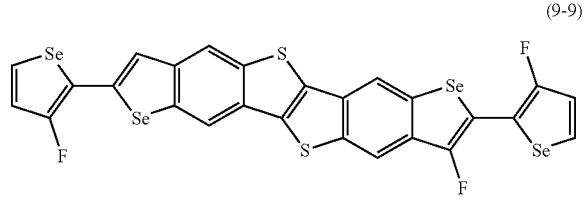
(9-10)
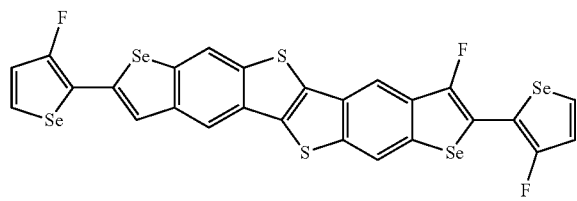
(9-11)
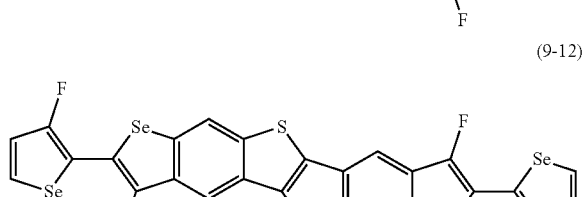
(9-12)
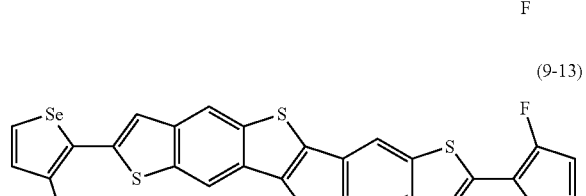
(9-13)
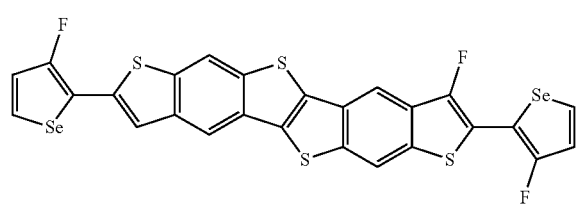
(9-14)
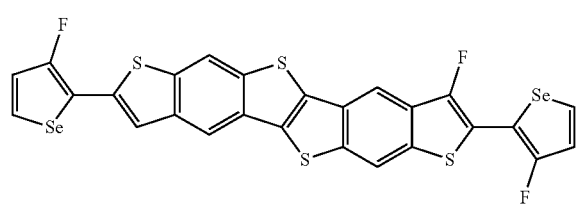
-continued
(9-15)
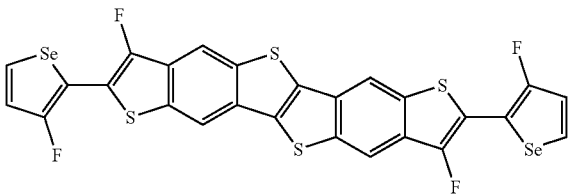
(9-16)
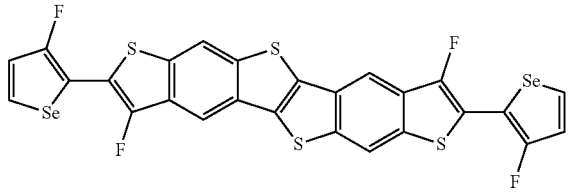
(9-17)
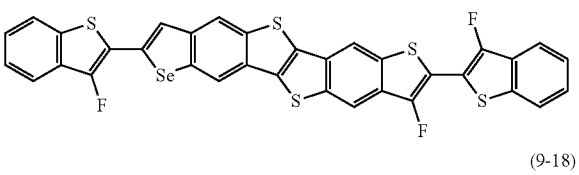
(9-18)
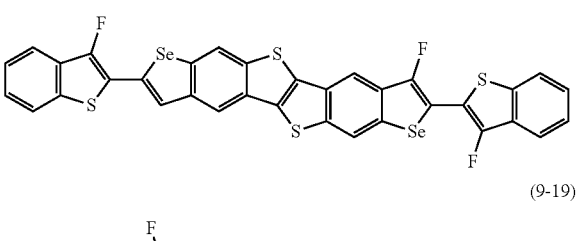
(9-19)
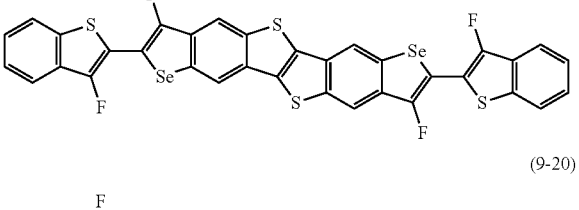
(9-20)
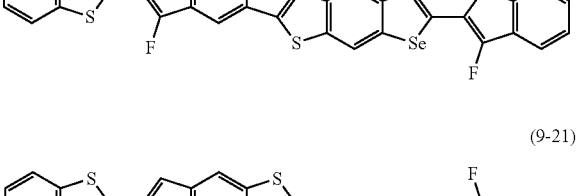
(9-21)
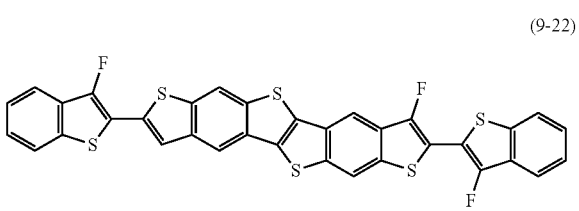
(9-22)
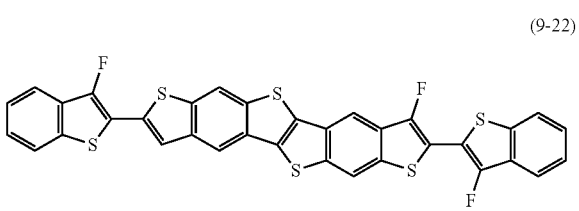

(9-23)
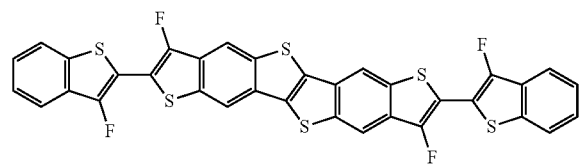
(9-24)
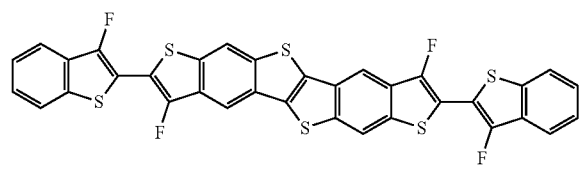
(9-25)
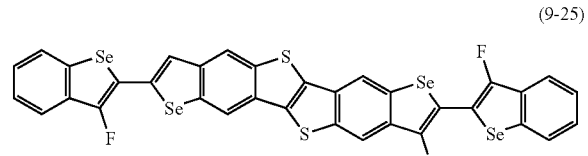
(9-26)
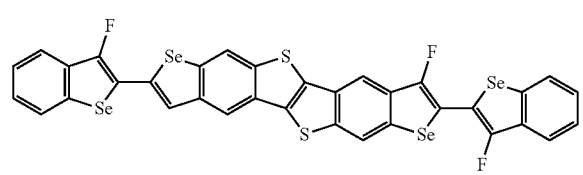
(9-27)
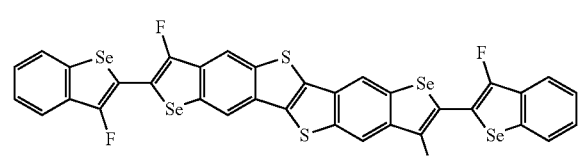
(9-28)
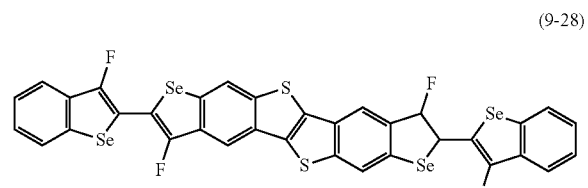
(9-29)
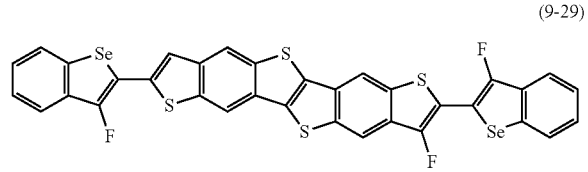
(9-30)
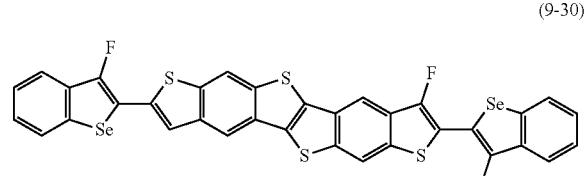
(9-31)
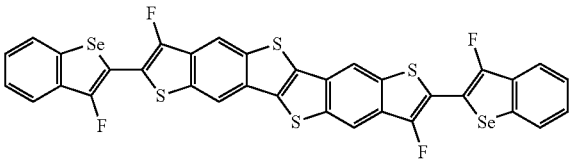
(9-32)
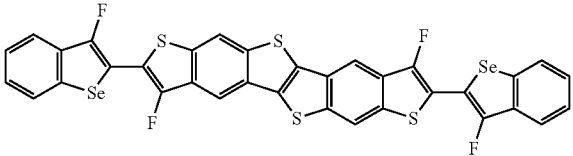
(9-33)
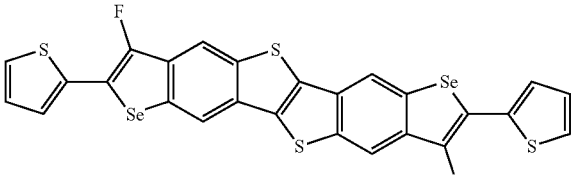
(9-34)
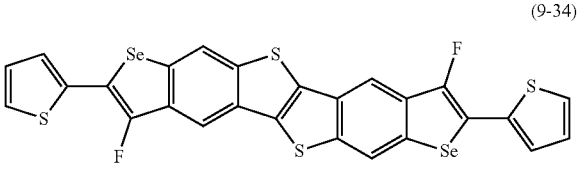
(9-35)
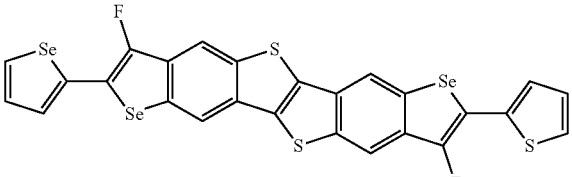
(9-36)
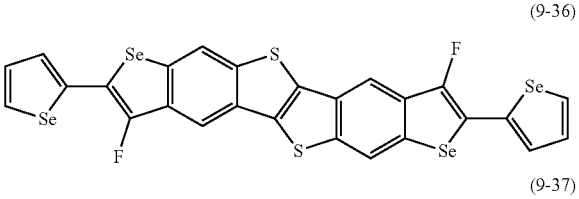
(9-37)
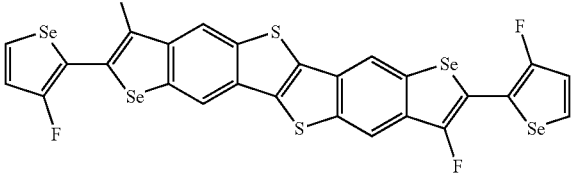
(9-38)
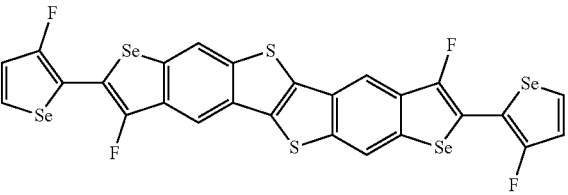

-continued (9-39)

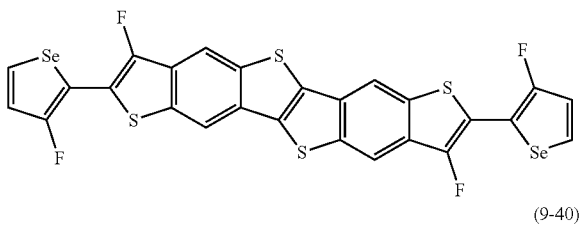

(9-40)

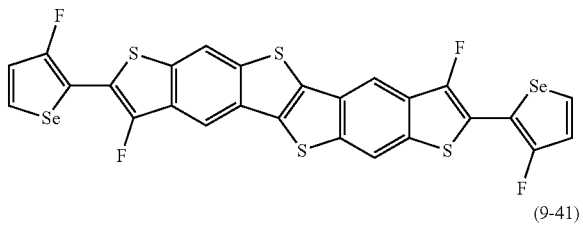

(9-41)

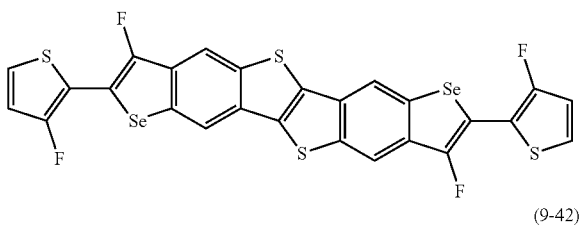

(9-42)

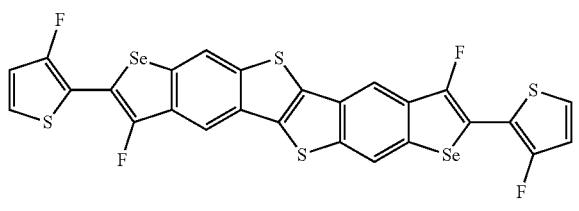

According to another embodiment, an organic thin film including the fused polycyclic heteroaromatic compound is provided.

According to another embodiment, a thin film transistor includes a gate electrode, a semiconductor overlapping with the gate electrode, and a source electrode and a drain electrode electrically connected to the organic semiconductor, wherein the semiconductor includes the fused polycyclic heteroaromatic compounds.

[Chemical Formula 1]

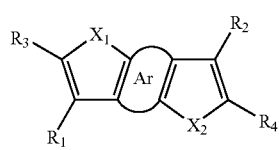

In Chemical Formula 1, $X_1$ and $X_2$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, Ar is a substituted or unsubstituted C6 to C30 aromatic ring, a substituted or unsubstituted C3 to C30 heteroaromatic ring, or a fused ring including the fused two or more rings, Ar is combined with an $X_1$-containing hetero ring and an $X_2$-containing hetero ring to provide a condensed polycyclic ring, $R_1$ and $R_2$ are independently hydrogen or a halogen atom, and $R_3$ and $R_4$ are independently a heterocyclic group including a heteroatom selected from N, S, Se, and Te, wherein the heteroatom is adjacent to carbon linked with the condensed polycyclic ring.

According to another embodiment, an electronic device including the organic thin film transistor is provided.

The electronic device may include a liquid crystal display (LCD), an organic light emitting diode device, an eletrophoretic device, an organic photoelectric device, and an organic sensor.

According to another embodiment, an electronic device including the organic thin film is provided.

According to the embodiment, a fused polycyclic heteroaromatic compound having improved charge mobility and dense molecular packing among and being easily synthesizable is provided. The fused polycyclic heteroaromatic compound has a conjugation structure but includes rings which are not fused one another and thus reinforces planarity among the adjacent rings and accordingly, may show improved charge mobility without extending a conjugation through a complex synthesis process or forming a core structure having an aryl group attached to the terminal end.

DETAILED DESCRIPTION

Figure 1:
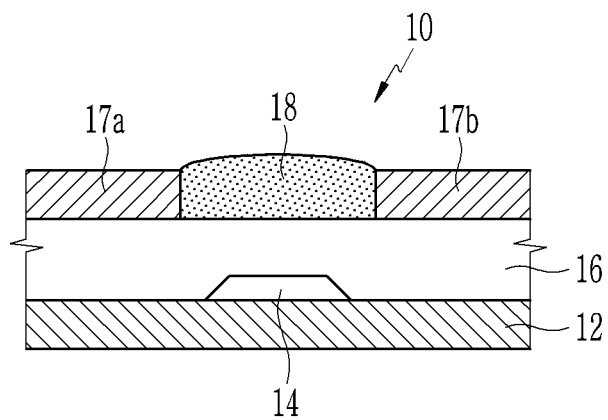
FIG. 1 is a schematic cross-sectional view of a transistor according to an embodiment.

Example embodiments will be hereinafter described in detail, and may be easily performed by a person skilled in the related art. However, this disclosure may be embodied in many different forms and is not construed as limited to the example embodiments set forth herein.

In the drawings, the thickness of layers, films, panels, regions, etc. are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, "combination thereof" may refer to a mixture, a stacked structure, a composite, an alloy, or the like.

As used herein, when a definition is not otherwise provided, "hetero" may refer to one including 1 to 4 heteroatoms selected from N, O, S, Si, and P in a ring. The total number of ring members may be 3 to 10. If multiple rings are present, each ring is independently aromatic, saturated, or partially unsaturated, and multiple rings, if present, may be fused, pendant, spirocyclic, or a combination thereof. "Heterocycloalkyl group" may be at least one non-aromatic ring including a heteroatom, and "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, and the like).

"Alkenyl group" may refer to a linear or branched saturated monovalent hydrocarbon group including at least one carbon-carbon double bond (e.g., an ethenyl group).

"Alkynyl group" may refer to a linear or branched saturated monovalent hydrocarbon group including at least one carbon-carbon (e.g., ethynyl group).

"Alkoxy group" may refer to an alkyl group that is linked via an oxygen, e.g., a methoxy, an ethoxy, and a sec-butyloxy group.

"Aryl group" may refer to a monovalent functional group formed by the removal of one hydrogen atom from one or more rings of an arene, e.g., phenyl or naphthyl. The arene may refer to a hydrocarbon group having an aromatic ring, and includes monocyclic and polycyclic hydrocarbon groups wherein the additional ring(s) of the polycyclic hydrocarbon group may be aromatic or nonaromatic.

"Aryloxy group" may refer to an aryl group that is linked via an oxygen, and the aryl group is the same as described above.

"Arylalkyl group" may refer to an aryl group where at least one hydrogen is substituted with a lower alkylene, e.g., methylene, ethylene, propylene, and the like. For example, the "arylalkyl group" may be a benzyl group or a phenyl-ethyl group.

"Cycloalkyl group" may refer to a monovalent functional group having one or more saturated rings in which all ring members are carbon, e.g., a cyclopentyl group and a cyclohexyl group.

"Cycloalkenyl group" may refer to a monovalent functional group including at least one ring having a carbon-carbon double bond, wherein all ring members are carbon, e.g., a cyclopentenyl group or a cyclohexenyl group.

"Cycloalkynyl group" may refer to a stabilized aliphatic monocyclic or multicyclic functional group including at least one carbon-carbon triple bond.

"Heteroarylalkyl group" may refer to an alkyl group where at least one hydrogen is replaced by a heteroaryl group wherein the alkyl group is the same as described above.

"Alkylheteroaryl group" may refer to a heteroaryl group where at least one hydrogen is replaced by an alkyl group wherein the heteroaryl group is the same as described above.

As used herein, when a definition is not otherwise provided, "aromatic ring" may refer to a functional group in which all atoms in the cyclic functional group have a p-orbital, wherein these p-orbitals are conjugated. For example, the aromatic ring may be a C6 to C20 aryl group.

As used herein, when a definition is not otherwise provided, "heteroaromatic ring" may refer to a functional group including a heteroatom selected from N, O, and S in a ring in which all atoms in the cyclic functional group have a p-orbital, wherein the p-orbital is conjugated. For example, the heteroaromatic ring may be a C2 to C20 heteroaryl group.

As used herein, when a definition is not otherwise provided, the term "alicyclic ring" may refer to non-conjugated ring, for example a C3 to C20 cycloalkyl group, a C3 to C20 heterocycloalkyl group, a C3 to C20 cycloalkenyl group, a C3 to C20 heterocycloalkenyl group, and the like.

As used herein, when a definition is not otherwise provided, "substituted" refers to replacement of hydrogen of a functional group or a compound by a functional group selected from a halogen (—F, —Cl, —Br, or —I) group, a C1 to C30 linear or branched alkyl group, for example a C1 to C10 linear or branched alkyl group, a C2 to C30 linear or branched alkenyl group, for example a C2 to C10 linear or branched alkenyl group, a C2 to C30 linear or branched alkynyl group, for example a C2 to C10 linear or branched alkynyl group, a C6 to C30 aryl group, for example a C6 to C12 aryl group, a C2 to C30 heteroaryl group, for example a C2 to C12 heteroaryl group, a C3 to C30 cycloalkyl group, a C1 to C20 fluoroalkyl group, a C1 to C20 perfluoroalkyl group ($C_nF_{2n+1}$), a C1 to C30 linear or branched alkoxy group, a C3 to C30 cycloalkoxy group, a C2 to C30 linear or branched alkoxyalkyl group, a C4 to C30 cycloalkoxyalkyl group, a cyano group, an amino group (—NRR', wherein R and R' are independently hydrogen or a C1 to C10 alkyl group), an amidino group (—C(=NH)NH$_2$), a nitro group (—NO$_2$), an amide group (—C(=O)N(H)R, wherein R is hydrogen or a C1 to C10 alkyl group), an aldehyde group (—C(=O)H), a hydroxy group (—OH), sulfonyl group (—S(=O)$_2$R, wherein R is independently hydrogen or a C1 to C10 alkyl group), and a carbamate group (—NHC(=O)OR, wherein R is a C1 to C10 alkyl group) provided that normal valence is not exceeded.

According to an embodiment, a fused polycyclic heteroaromatic compound represented by Chemical Formula 1 is provided.

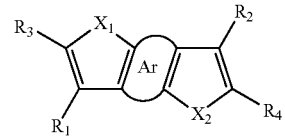

[Chemical Formula 1]

In Chemical Formula 1, $X_1$ and $X_2$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, Ar is a substituted or unsubstituted C6 to C30 aromatic ring, a substituted or unsubstituted C3 to C30 heteroaromatic ring, or a fused ring including the fused two or more rings, Ar is combined with an $X_1$-containing hetero ring and an $X_2$-containing hetero ring to provide a condensed polycyclic ring, $R_1$ and $R_2$ are independently hydrogen or a halogen atom, and $R_3$ and $R_4$ are independently a heterocyclic group including a heteroatom selected from N, S, Se, and Te, wherein the heteroatom is adjacent to carbon linked with the condensed polycyclic ring.

The fused polycyclic heteroaromatic compound represented by Chemical Formula 1 consists of a core moiety and a substituent moiety including a heterocyclic group respectively disposed at both terminal ends of the core moiety. In an embodiment, the core moiety indicates a condensed polycyclic ring wherein Ar is linked with an $X_1$-containing hetero ring and an $X_2$-containing hetero ring, and the substituent moiety indicates a heterocyclic group respectively disposed at $R_3$ and $R_4$ of the core moiety. The core moiety and the substituent moiety respectively have a two dimensional planar structure of aromatic ring groups.

In an embodiment, the substituent moiety may be represented by Chemical Formula 2-1 or Chemical Formula 2-2. That is, $R_3$ and $R_4$ of Chemical Formula 1 may independently be one of heterocyclic groups represented by Chemical Formula 2-1 and Chemical Formula 2-2.

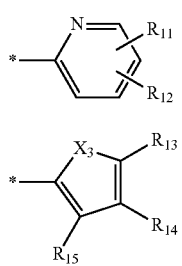

[Chemical Formula 2-1]

[Chemical Formula 2-2]

In Chemical Formula 2-1 and Chemical Formula 2-2, $X_3$ is S, Se, or Te, $R_{11}$ to $R_{14}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{15}$ is hydrogen or a halogen atom, $R_{11}$ and $R_{12}$ are independently present alone or combined to provide a ring, $R_{13}$ and $R_{14}$ are independently present alone or adjacent two thereof are combined to provide a ring, and

* is a linking point with the condensed polycyclic ring of Chemical Formula 1.

According to an embodiment, the heteroatom in the heterocyclic group of the substituent moiety is disposed adjacent to carbon where linked with the condensed polycyclic ring. When the heteroatom in the heterocyclic group is disposed at the above site, a molecular interaction of the core moiety and the substituent moiety may be increased, and a structure of promoting a molecular alignment may be formed. Specifically, generation of a bond rotation in a single bond of linking the heterocyclic group with an aromatic group of the core moiety may be suppressed. Accordingly, the condensed polycyclic ring and the heterocyclic group represented by Chemical Formula 2-1 or Chemical Formula 2-2 may be disposed on a substantially equivalent plane and have an overall compact planar-type molecular structure.

According to an embodiment, $R_3$ and $R_4$ may have the same heterocyclic group. Herein, since symmetry between the core moiety and the substituent moiety is improved, the fused polycyclic heteroaromatic compound may have a more compact planar-type molecular structure. However, the embodiment is not necessarily limited thereto, but $R_3$ and $R_4$ may be independently substituted with different heterocyclic groups (e.g., a heterocyclic group represented by Chemical Formula 2-1 and a heterocyclic group represented by Chemical Formula 2-2).

According to an embodiment, the Ar may have four to eight rings. In other words, the core moiety may have six to ten rings in total.

According to an embodiment, the condensed polycyclic ring of the core moiety may be represented by one of Chemical Formula 3-1 to Chemical Formula 3-16

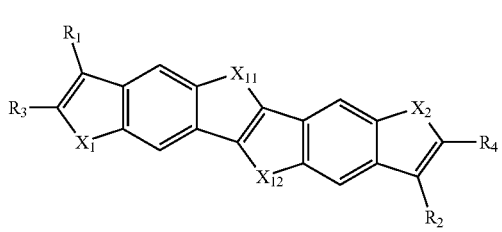

(3-1)

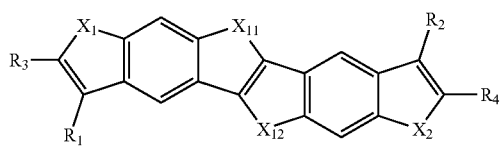

(3-2)

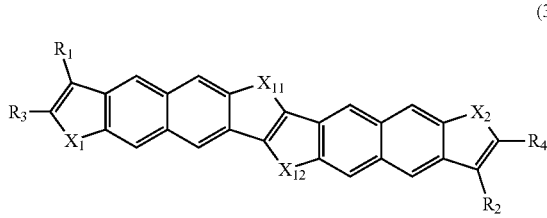

(3-3)

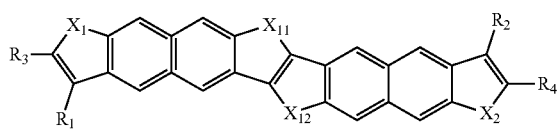

(3-4)

-continued
(3-5)
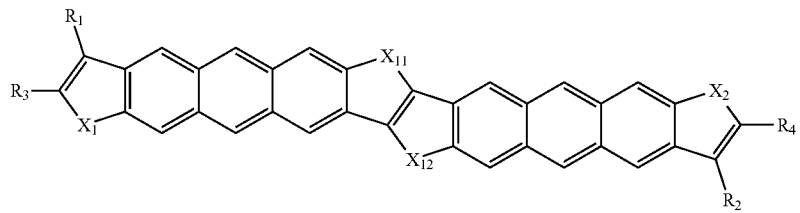
(3-6)
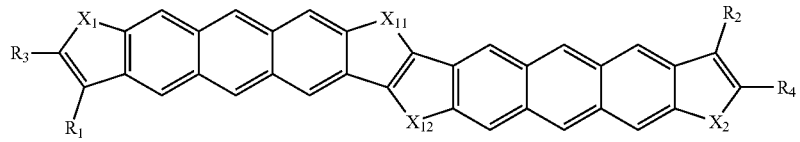
(3-7)
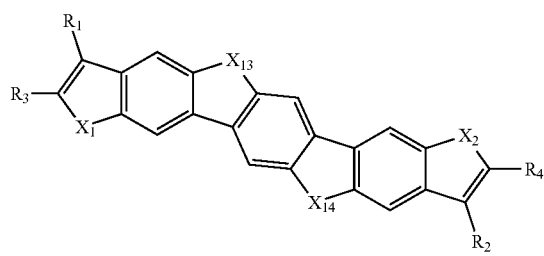
(3-8)
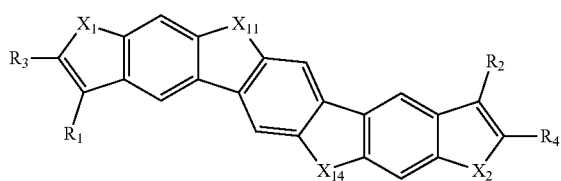
(3-9)
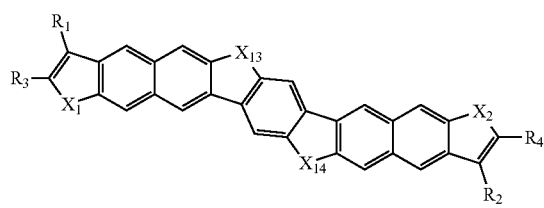
(3-10)
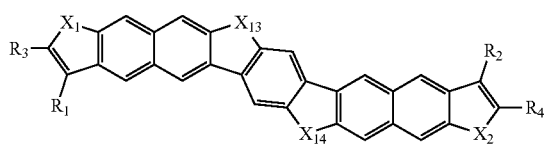
(3-11)
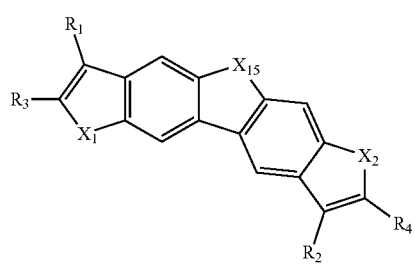
(3-12)
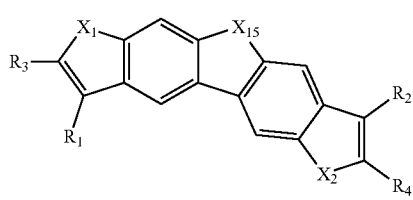
(3-13)
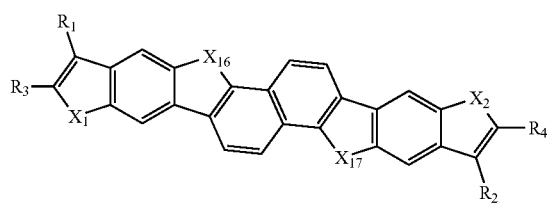
(3-14)
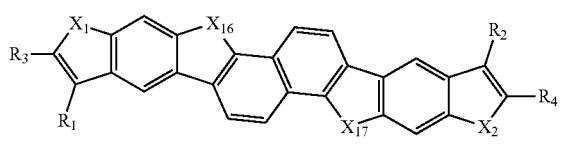
(3-15)
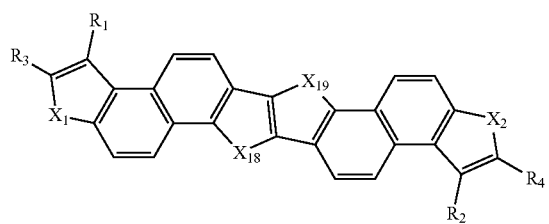
(3-16)
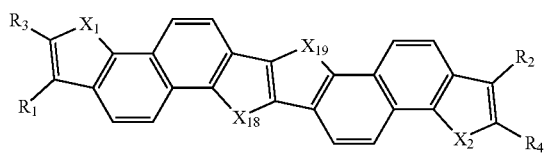

In Chemical Formula 3-1 to Chemical Formula 3-16, $X_1$, $X_2$, $R_1$, $R_2$, $R_3$, and $R_4$ are the same as in Chemical Formula 1, $X_{11}$ to $X_{19}$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof.

In general, mobility of an organic semiconductor material tends to be improved, as the number of a fused ring in a core moiety is increased. However, as the number of a fused ring in a core moiety is increased, there is a problem of requiring a more complex synthesis route and thus deteriorating processability. In order to solve this problem, research on a method of substituting an aromatic organic group and the like instead of the heterocyclic group at both terminal ends of the core moiety is being made, but these non-heterocyclic groups may have a bond rotation with the core moiety and thus rarely secure planarity and inevitably deteriorate device characteristics.

On the contrary, the fused polycyclic heteroaromatic compound according to an embodiment may have a more compact planar-type molecular structure by suppressing a bond rotation of a substituent moiety, even though a core moiety is linked with the substituent moiety through a single bond, and thus adjusting the core moiety and the substituent moiety to be disposed on a substantially equivalent plane. Accordingly, the fused polycyclic heteroaromatic compound according to an embodiment may have a substantial conjugation extension effect by linking a substituent moiety of a heterocyclic group where a heteroatom is designated with a particular position of the core moiety without increasing the number of fused ring of the core moiety.

When the fused polycyclic heteroaromatic compound is applied to an electronic device, the fused polycyclic heteroaromatic compound contributes to molecular packing and stacking as well as a uniform and stable oxidation potential and thus shows higher charge mobility and in addition, may be easily synthesized and thus usefully used as a semiconductor material, an electron transport material, an active layer material, and the like.

As one way of suppressing the bond rotation of a substituent moiety, $R_{11}$ to $R_{15}$ may be independently hydrogens. Herein, as the substituent moiety has a stable three dimensional structure, generation of a steric hindrance effect of the substituent moiety with terminal ends of the adjacent core moiety may be reduced or minimized, through which generation of a bond rotation may be suppressed from a single bond of linking the heterocyclic group with an aromatic group of the core moiety.

Examples of the condensed polycyclic hetero aromatic compound satisfying the above way may be a condensed polycyclic hetero aromatic compound represented by Chemical Formula 4.

[Chemical Formula 4]

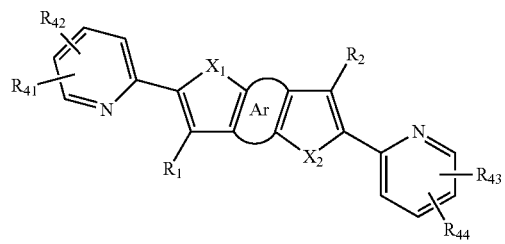

In Chemical Formula 4, $X_1$, $X_2$, Ar, $R_1$, and $R_2$ are the same as in Chemical Formula 1, $R_{41}$ to $R_{44}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{41}$ and $R_{42}$ are independently present alone or adjacent two thereof are combined to provide a ring, and $R_{43}$ and $R_{44}$ are independently present alone or adjacent two thereof are combined to provide a ring.

Specific examples of the compound represented by Chemical Formula 4 may be Chemical Formulae 5-1 to 5-36. However, an embodiment is not necessarily limited thereto but may include various compounds satisfying Chemical Formula 4.

(5-1)

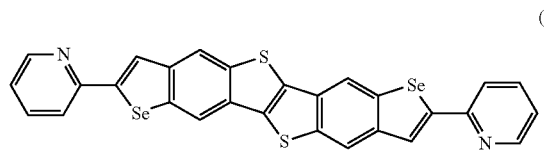

(5-2)

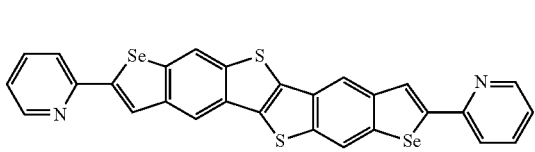

(5-3)

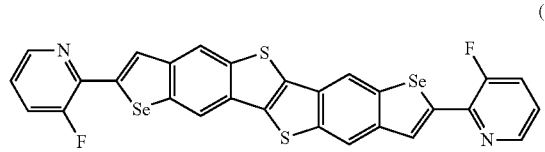

(5-4)

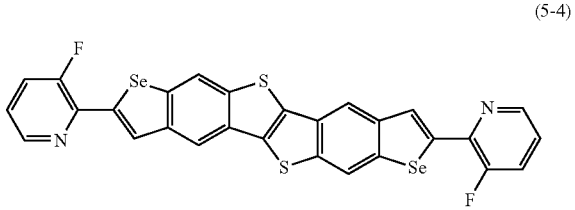

(5-5)
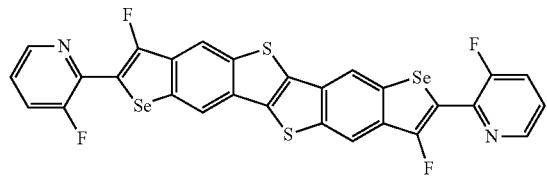
(5-6)
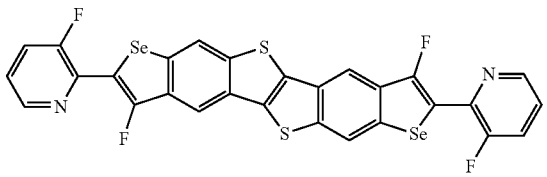
(5-7)
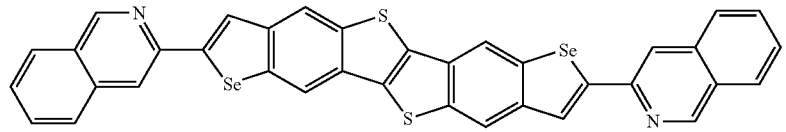
(5-8)
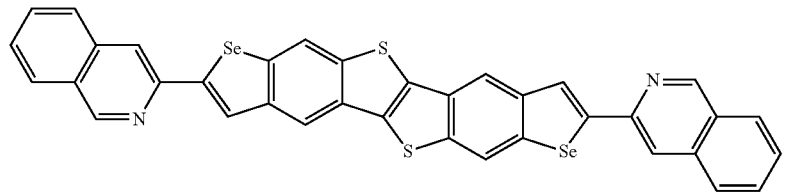
(5-9)
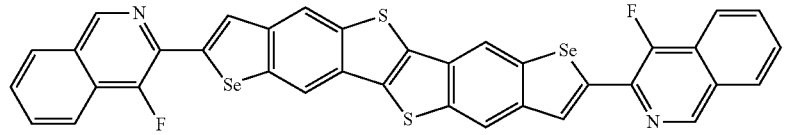
(5-10)
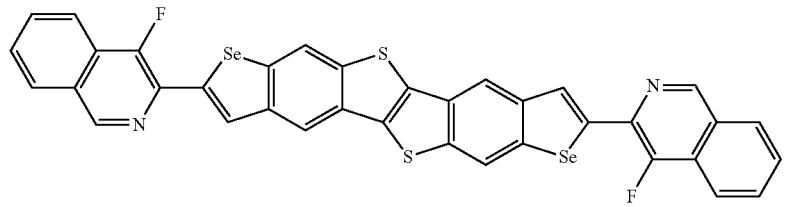
(5-11)
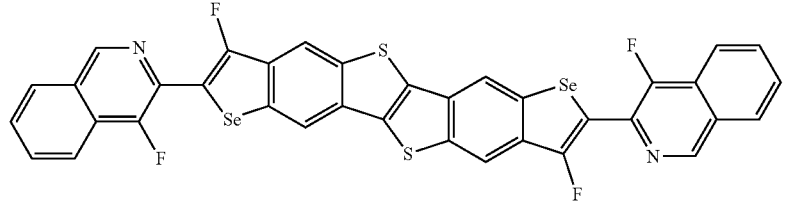
(5-12)
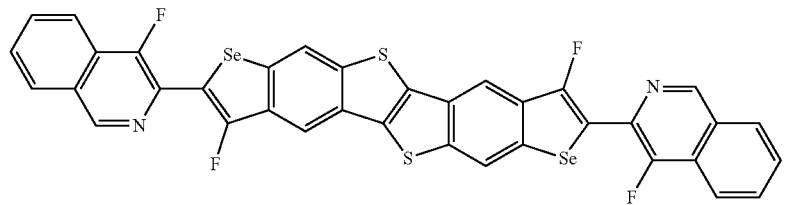
(5-13)
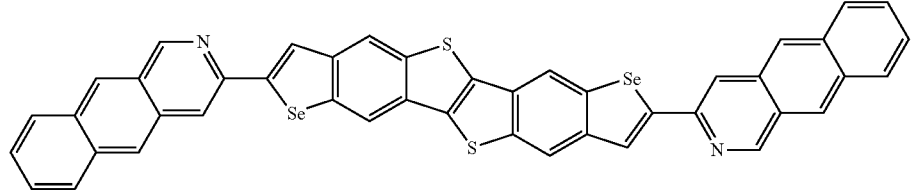

-continued
(5-14)
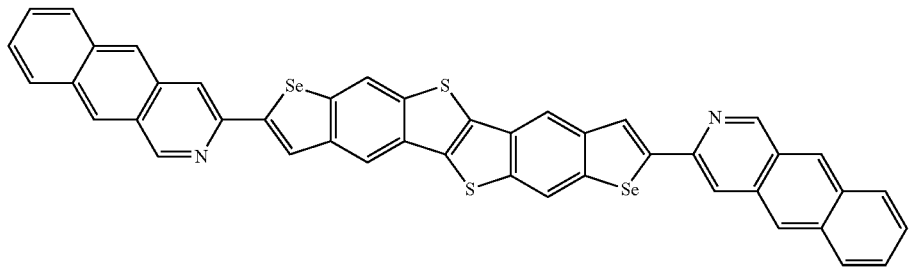
(5-15)
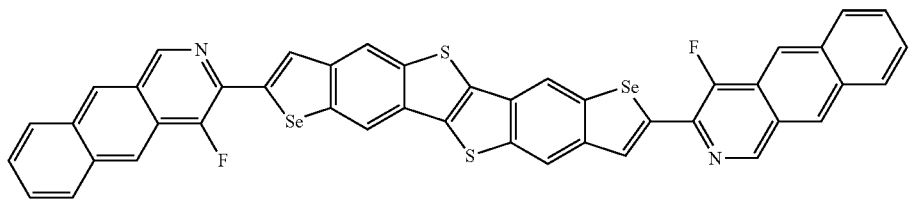
(5-16)
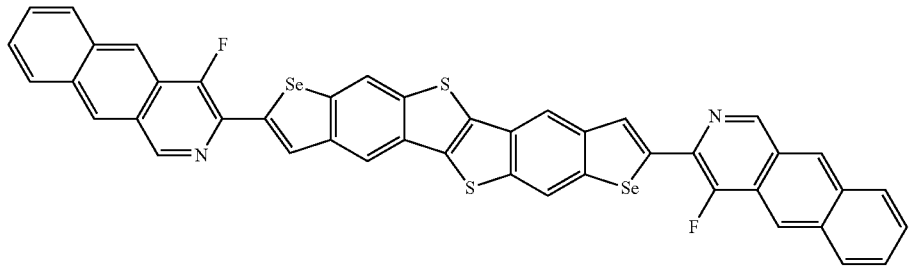
(5-17)
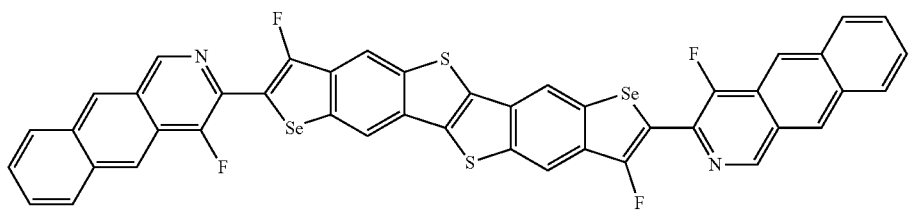
(5-18)
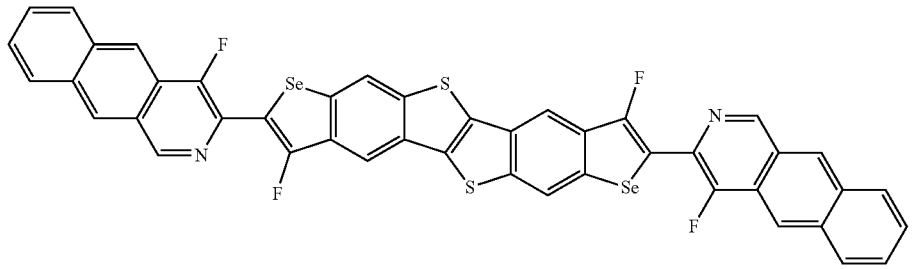
(5-19)
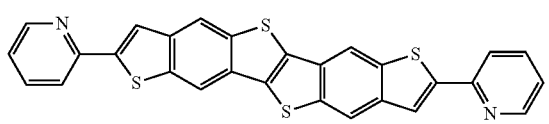
(5-20)
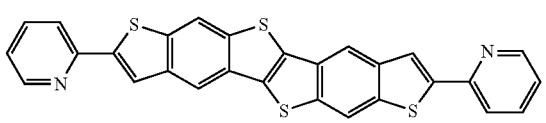
(5-21)
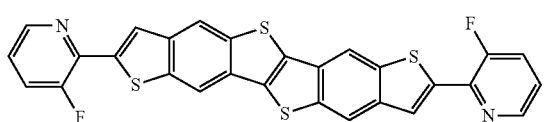
(5-22)
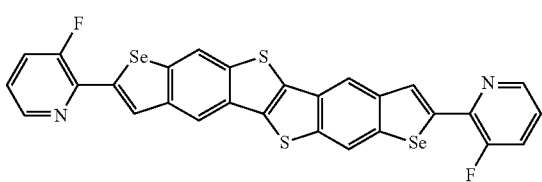

-continued
(5-23)
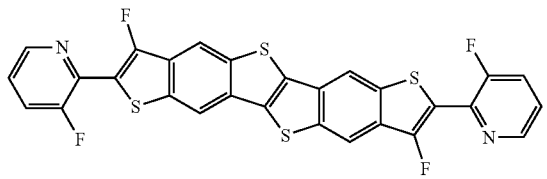
(5-24)
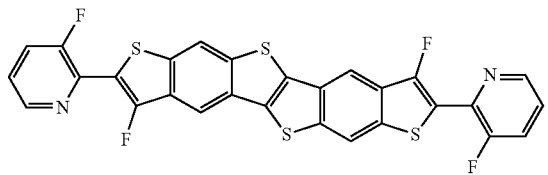
(5-25)
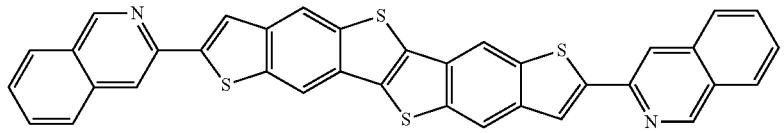
(5-26)
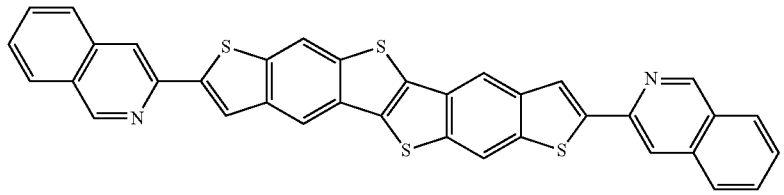
(5-27)
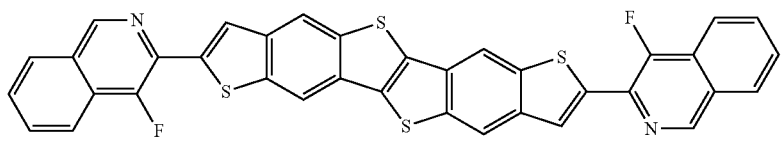
(5-28)
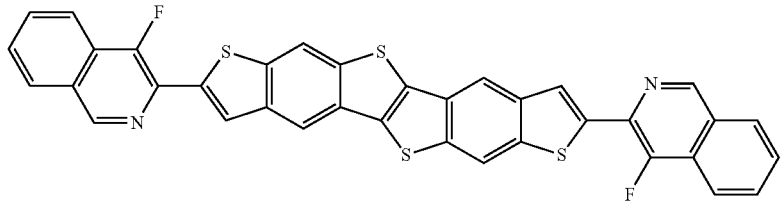
(5-29)
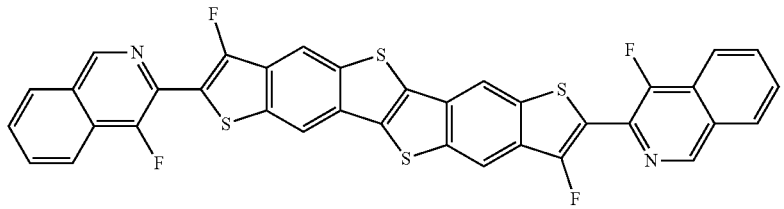
(5-30)
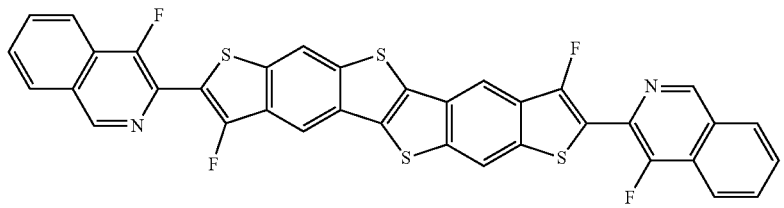
(5-31)
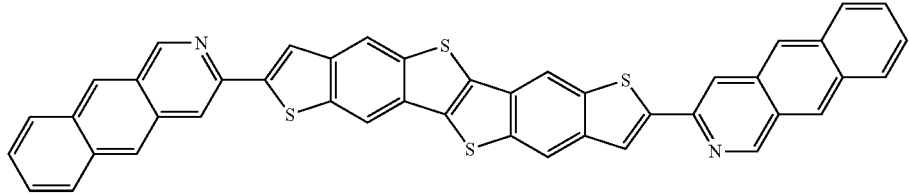

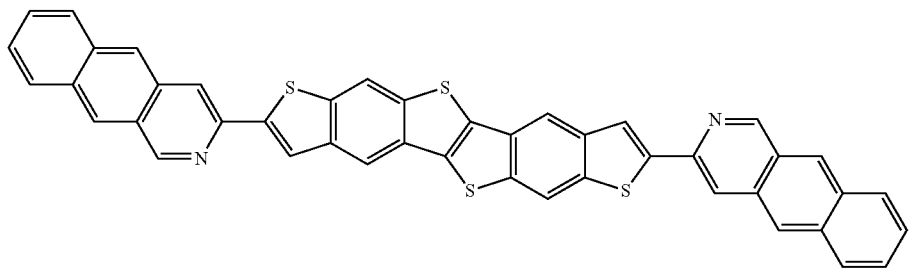
(5-32)
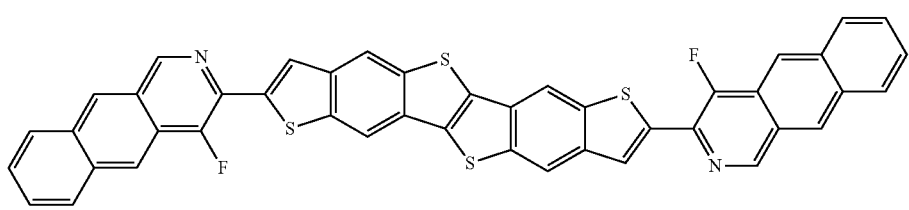
(5-33)
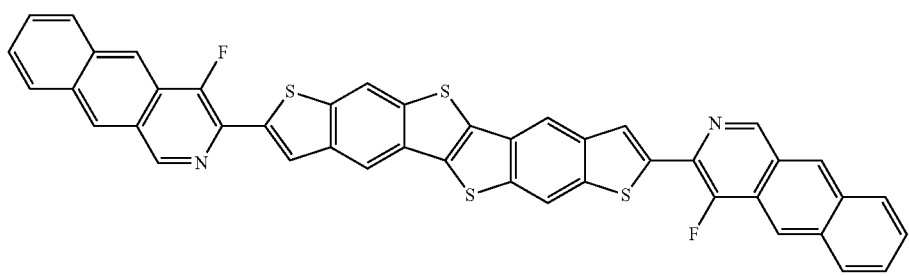
(5-34)
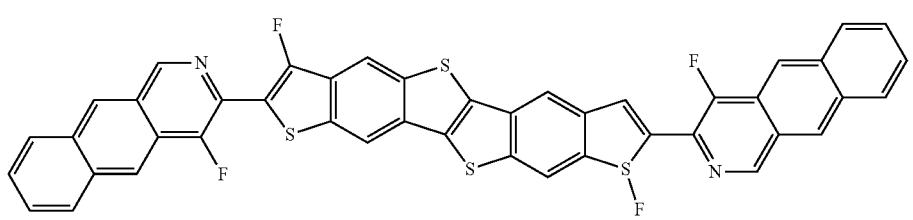
(5-35)
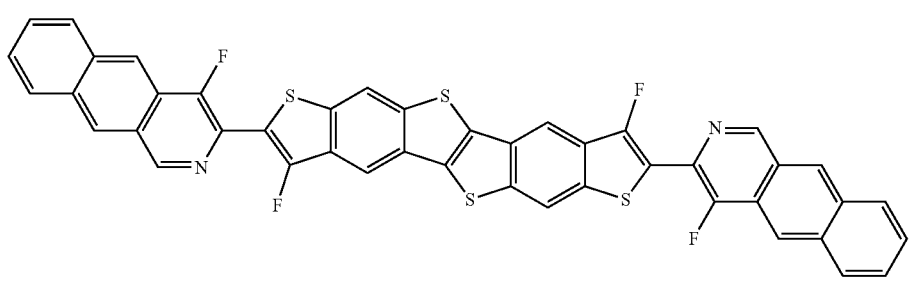
(5-36)

On the other hand, another example of the condensed polycyclic hetero aromatic compound may include a condensed polycyclic hetero aromatic compound represented by Chemical Formula 6.

[Chemical Formula 6]

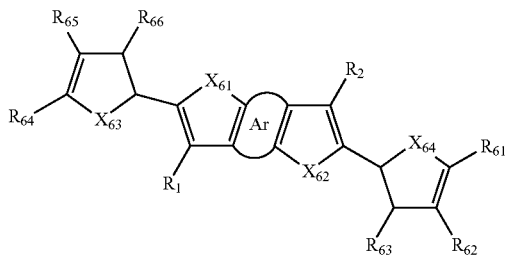

In Chemical Formula 6,

Ar, $R_1$, and $R_2$ are the same as in Chemical Formula 1, $X_{61}$ to $X_{64}$ are independently S or Se, $R_{61}$, $R_{62}$, $R_{64}$, and $R_{65}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{63}$ and $R_{66}$ are independently hydrogen or a halogen atom, $R_{61}$ and $R_{62}$ are independently present alone or combined to provide a ring, and $R_{64}$ and $R_{65}$ are independently present alone or combined to provide a ring.

Specific examples of the compound represented by Chemical Formula 6 may be Chemical Formulae 7-1 to 7-24. However, an embodiment is not necessarily limited thereto but includes various compounds satisfying and the above way and a condition of Chemical Formula 6.

(7-1)

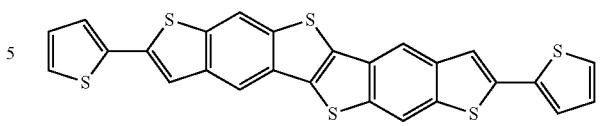

(7-2)

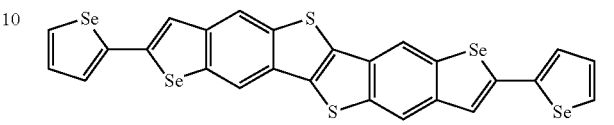

(7-3)

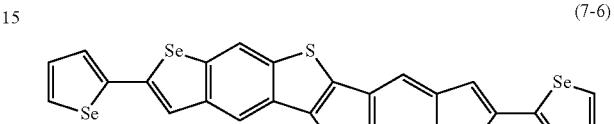

(7-4)

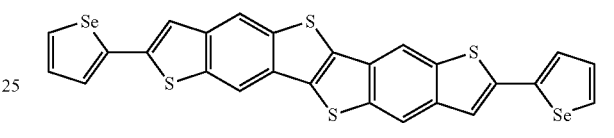

(7-5)

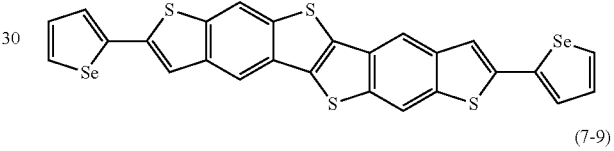

(7-6)

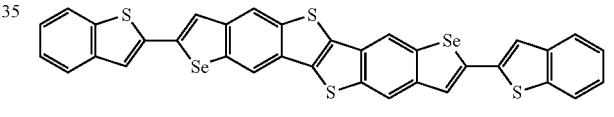

(7-7)

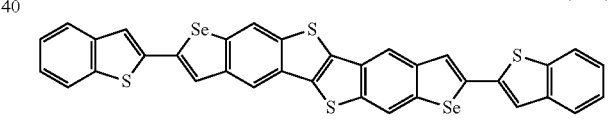

(7-8)

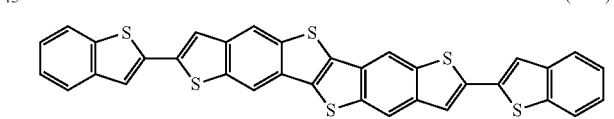

(7-9)

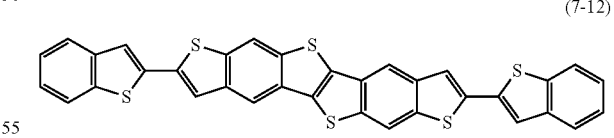

(7-10)

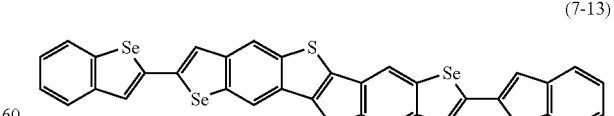

(7-11)

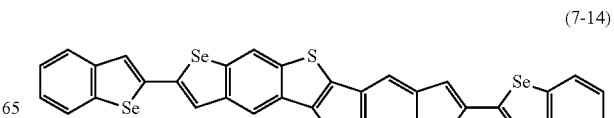

(7-12)

(7-13)

(7-14)

On the other hand, as another way of suppressing the bond rotation of the substituent moiety, at least either one of $R_1$ and $R_2$ may be a halogen atom, for example, $R_{15}$ may be a halogen atom, and at least either one of $R_1$ and $R_2$ may be a halogen atom. When a heterocyclic group represented by Chemical Formula 2-2 is disposed at at least one of $R_3$ and $R_4$ of a core moiety, but a halogen atom is disposed at $R_{15}$, and a halogen atom is disposed at either one of $R_1$ and $R_2$ at the terminal end of the core moiety, which is adjacent to Chemical Formula 2-2, a molecular attraction between $X_3$ inside Chemical Formula 2-2 and $R_1$ or $R_2$ adjacent thereto may be formed. For example, when $X_3$ is S, and $R_1$ or $R_2$ adjacent to Chemical Formula 2-2 is F, an interaction between S and F may be generated. In this way, the molecular interaction generated between the core moiety and the substituent moiety may suppress generation of a bond rotation from a single bond of linking the heterocyclic group with an aromatic group of the core moiety.

On the other hand, examples of the condensed polycyclic hetero aromatic compound satisfying the above way may be a condensed polycyclic hetero aromatic compound belonging to a condensed polycyclic hetero aromatic compound represented by Chemical Formula 6 and represented by one of Chemical Formulae 8-1 to 8-20.

However, an embodiment is not necessarily limited thereto but may include various compounds simultaneously satisfying the above way and a condition of Chemical Formula 6.

-continued (8-3)
(8-4)
(8-5)
(8-6)
(8-7)
(8-8)
(8-9)
(8-10)
(8-11)
(8-12)
(8-13)
(8-14)
(8-15)
(8-16)

-continued (8-17)
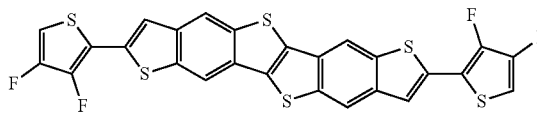

(8-18)
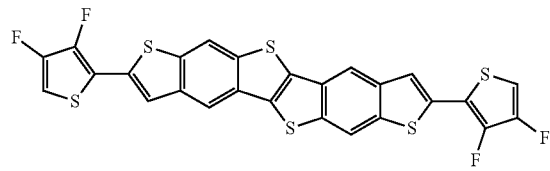

(8-19)
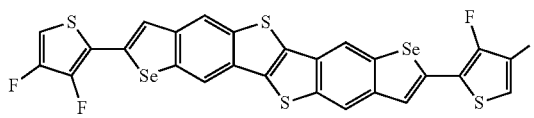

(8-20)
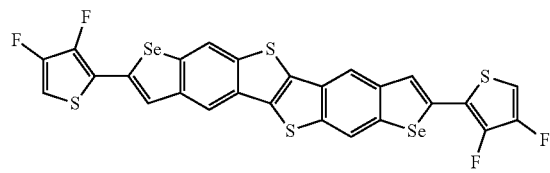

On the other hand, another example of the condensed polycyclic hetero aromatic compound satisfying the way may be a condensed polycyclic hetero aromatic compound belonging to a condensed polycyclic hetero aromatic compound represented by Chemical Formula 6 and represented by one of Chemical Formulae 9-1 to 9-42.

However, an embodiment is not necessarily limited thereto but may include various compounds simultaneously satisfying the above way and a condition of Chemical Formula 6.

(9-1)
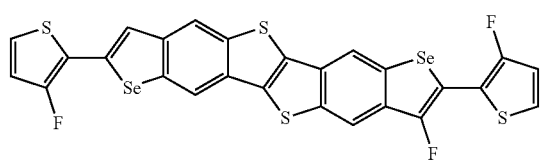

(9-2)
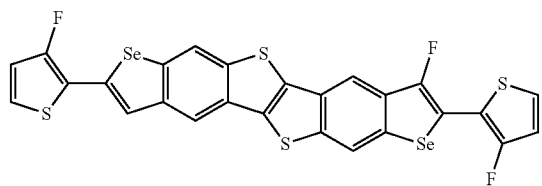

(9-3)
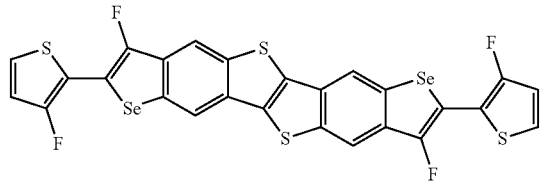

(9-4)
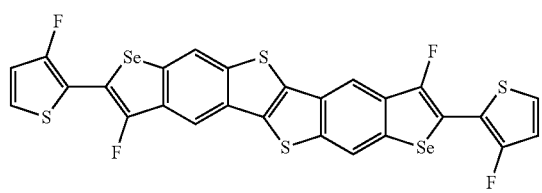

-continued (9-5)
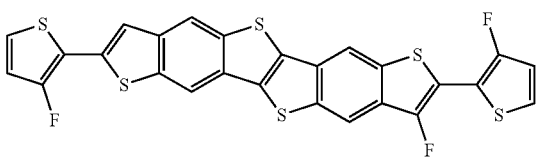

(9-6)
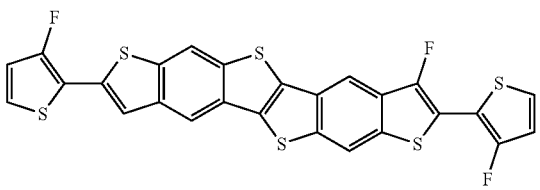

(9-7)
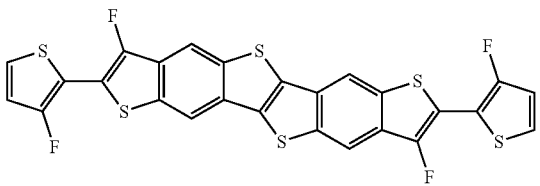

(9-8)
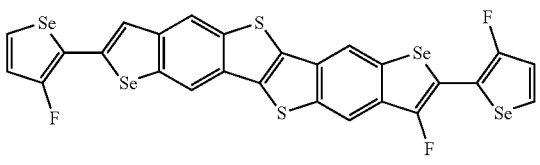

(9-9)

-continued
(9-10)
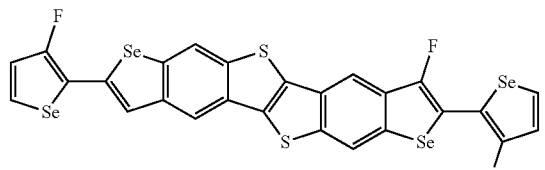
(9-11)
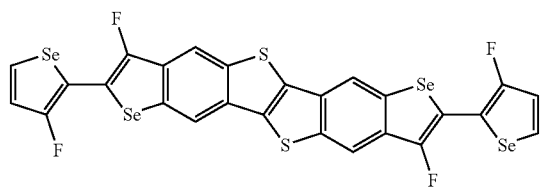
(9-12)
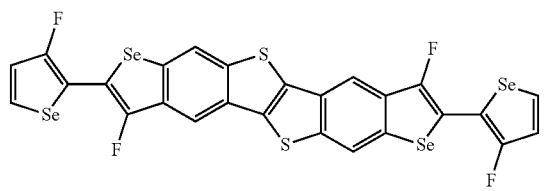
(9-13)
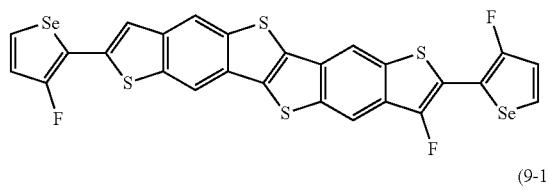
(9-14)
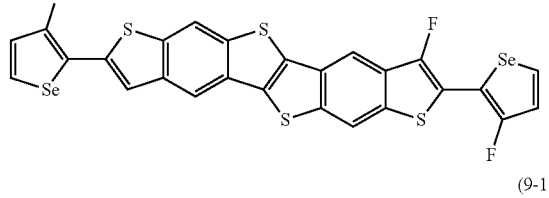
(9-15)
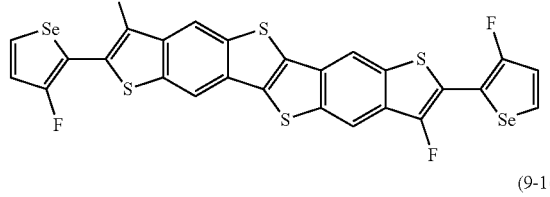
(9-16)
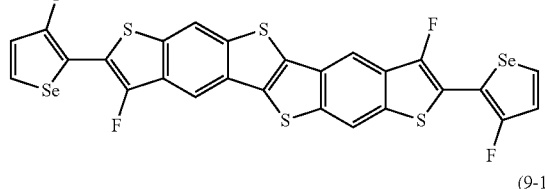
(9-17)
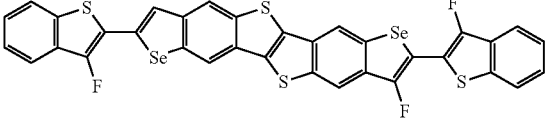
-continued
(9-18)
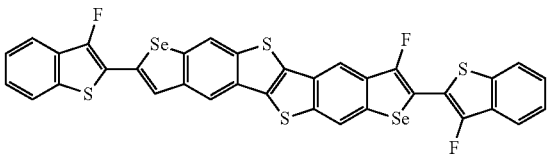
(9-19)
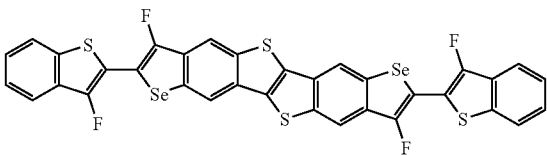
(9-20)
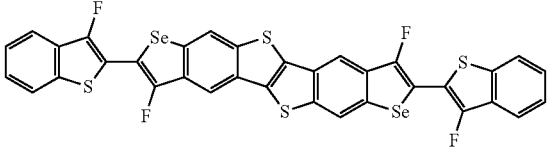
(9-21)
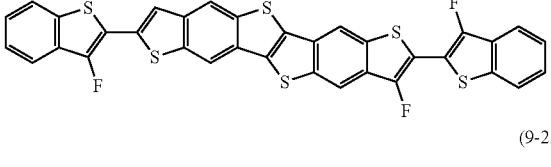
(9-22)
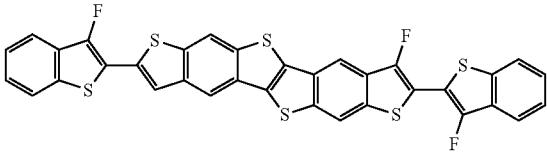
(9-23)
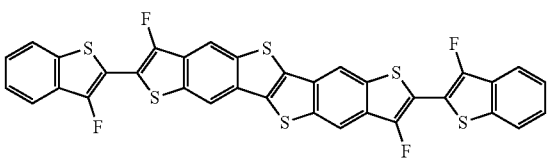
(9-24)
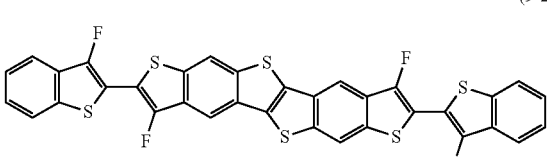
(9-25)
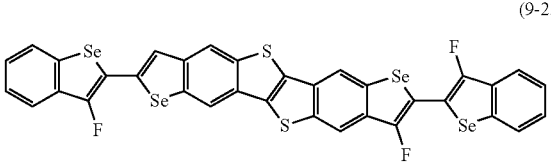
(9-26)
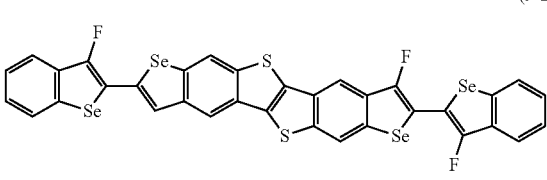

(9-27)
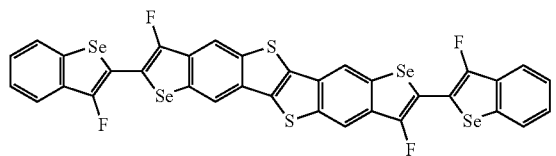
(9-28)
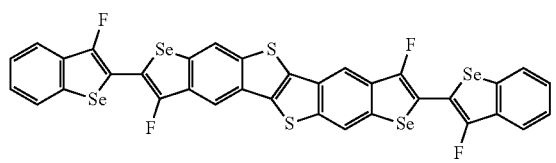
(9-29)
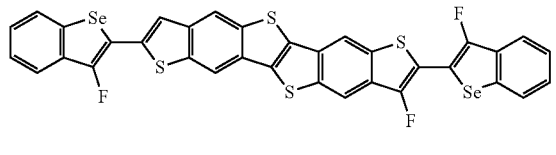
(9-30)
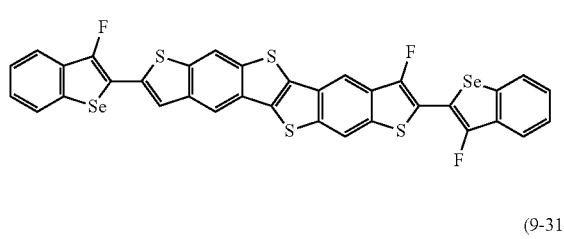
(9-31)
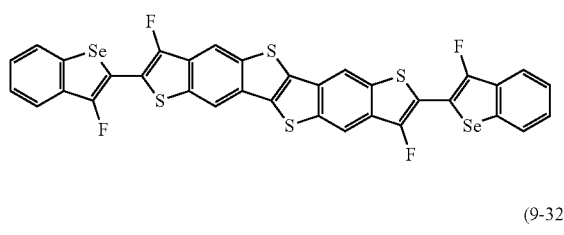
(9-32)
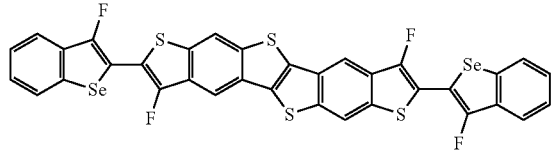
(9-33)
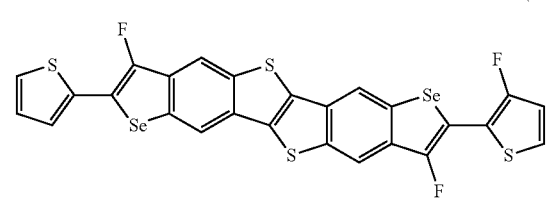
(9-34)
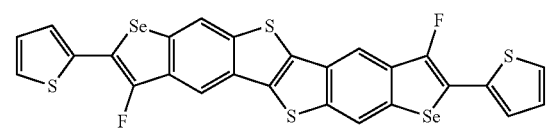
(9-35)
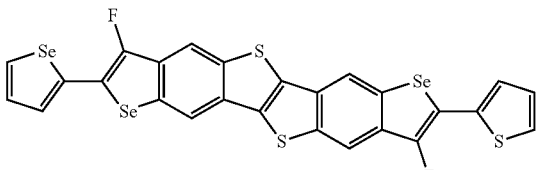
(9-36)
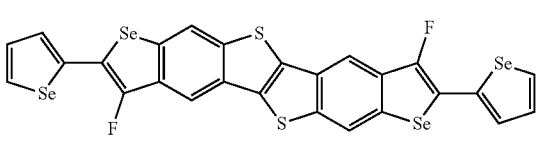
(9-37)
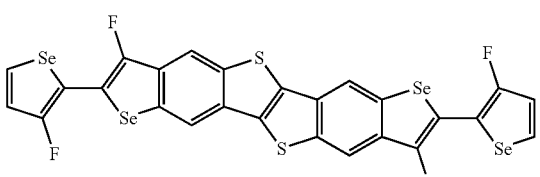
(9-38)
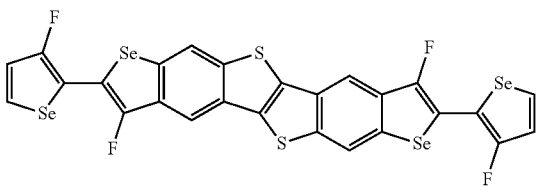
(9-39)
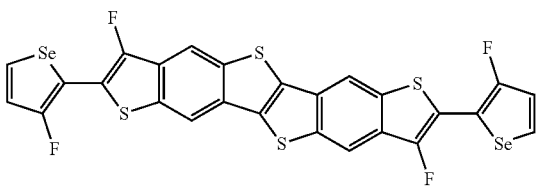
(9-40)
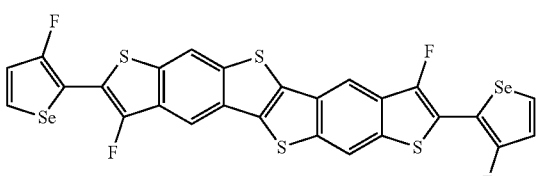
(9-41)
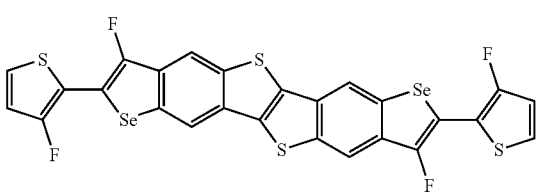

(9-42)

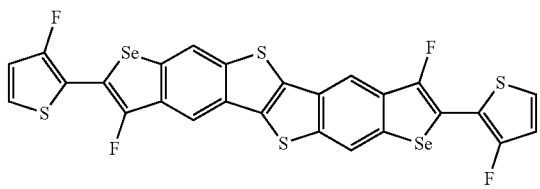

On the other hand, a tortional angle of a substituent moiety relative to a core moiety is calculated regarding a part of the fused polycyclic heteroaromatic compounds by using a Gaussian 09 program, and the result is shown in Table 1. Tortional angles of ref-1 to ref-6 for comparison are also shown in Table 1.

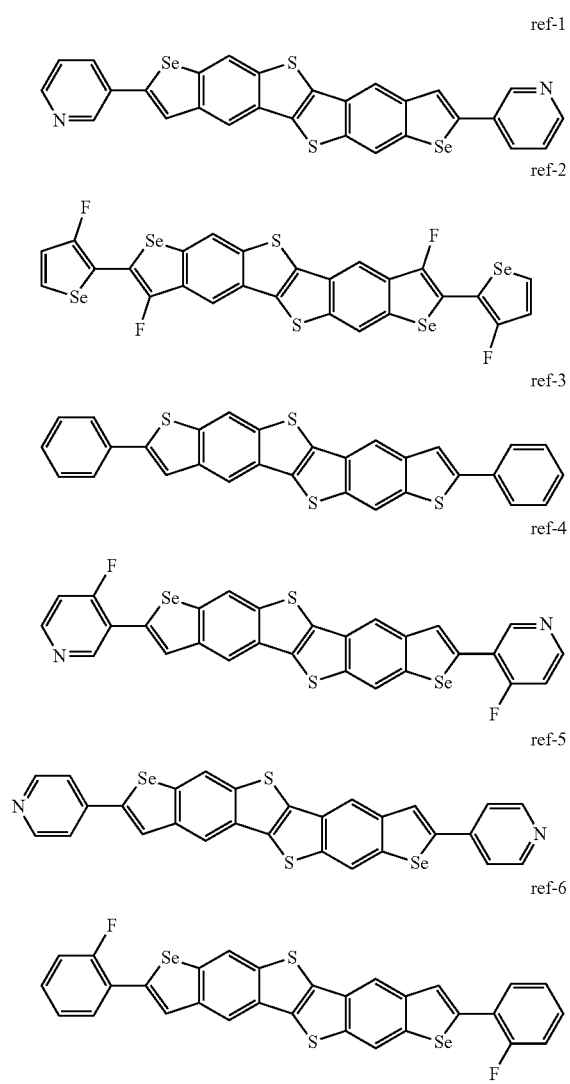

TABLE 1

| Chemical Formula | Tortional angle (°) |
|---|---|
| ref-1 | 33.6 |
| ref-2 | 32.7 |
| ref-3 | 32.7 |
| ref-4 | 29.8 |
| ref-5 | 27.81 |
| ref-6 | 24.8 |
| 7-6 | 23 |
| 7-2 | 21.8 |
| 8-14 | 0.03 |
| 9-34 | 0.03 |
| 9-36 | 0.03 |
| 8-16 | 0.02 |
| 9-12 | 0.02 |
| 8-4 | 0.02 |
| 8-18 | 0.02 |
| 8-20 | 0.02 |
| 8-8 | 0.02 |
| 8-2 | 0.02 |
| 9-38 | 0.02 |
| 9-40 | 0.02 |
| 9-42 | 0.02 |
| 5-2 | 0 |
| 5-4 | 0 |
| 9-4 | 0 |

Referring to Table 1, the fused polycyclic heteroaromatic compounds according to an embodiment show a lower tortional angle than those of conventional compounds (identified as ref-1 and ref-2 in Table 1), particularly, the fused polycyclic heteroaromatic compounds belonging to a group of Chemical Formula 8 and a group of Chemical Formula 9 show a much lower tortional angle than those of conventional compounds and a tortional angle substantially close to a plane (0 to 0.03°).

Example embodiments provide an organic thin film including the fused polycyclic heteroaromatic compound and an electronic device including the organic thin film.

The organic thin film according to example embodiments includes the fused polycyclic heteroaromatic compound, so it may be applied to an organic semiconductor layer for an electronic device, or a carrier transport layer such as a channel layer and/or an active layer. The electronic device including the same may have improved electrical properties such as higher charge mobility as well as improved processibility and/or workability.

The organic thin film may be manufactured by depositing the fused polycyclic heteroaromatic compound on a substrate according to any conventional method, or dissolving the fused polycyclic heteroaromatic compound in an organic solvent and then coating the same at room temperature according to a solution process. If required, heating treatment may be performed after the deposition or coating process to further enhance the densification and uniformity of the thin film.

For example, the organic solvent may include at least one kind of general organic solvent, for example, at least one kind of an aliphatic hydrocarbon solvent such as hexane, heptane, or the like; an aromatic hydrocarbon solvent such as toluene, pyridine, quinoline, anisole, mesitylene, xylene, or the like; a ketone-based solvent such as methyl isobutyl ketone, 1-methyl-2-pyrrolidinone, cyclohexanone, acetone, or the like; an ether-based solvent such as tetrahydrofuran, isopropyl ether, or the like; an acetate-based solvent such as ethyl acetate, butyl acetate, propylene glycol methyl ether acetate, or the like; an alcohol-based solvent such as isopropyl alcohol, butanol, or the like; an amide-based solvent such as dimethyl acetamide, dimethyl formamide, or the like; a silicone-based solvent; and a mixture of solvents. The amount of the fused polycyclic heteroaromatic compound dissolved in the organic solvent may be adequately selected and determined by a person of ordinary skill in the art, for example, in a range of about 0.01 wt % to about 50 wt % in the total solvent in view of solubility and/or coating property.

The method of providing an organic thin film may include thermal deposition, vacuum deposition, laser deposition, screen printing, printing, imprinting, spin casting, dipping, ink jetting, roll coating, flow coating, drop casting, spray coating, roll printing, and the like, but is not limited thereto. The heat treatment may be performed at about 80 to about 250° C. for about 1 minute to about 2 hours, but is not limited thereto.

A thickness of the organic thin film may be adjusted according to the usage and the case considering the kinds of the used compound and solvent by a person of ordinary skill in the art, and is for example, in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, and/or a sensor, and the organic thin film may be applied to each device according to conventional processes commonly known in the art.

For example, the transistor includes: a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by depositing the fused polycyclic heteroaromatic compound or coating a composition including the fused polycyclic heteroaromatic compound or the fused polycyclic heteroaromatic compound and the polymer by a solution process, e.g., a screen printing method, a printing method, a spin coating method, a dipping method, an inkjet method, etc. When the active layer is formed by the solution process, the process cost may be reduced, and a relatively wide area device may be effectively manufactured.

Figure 2:
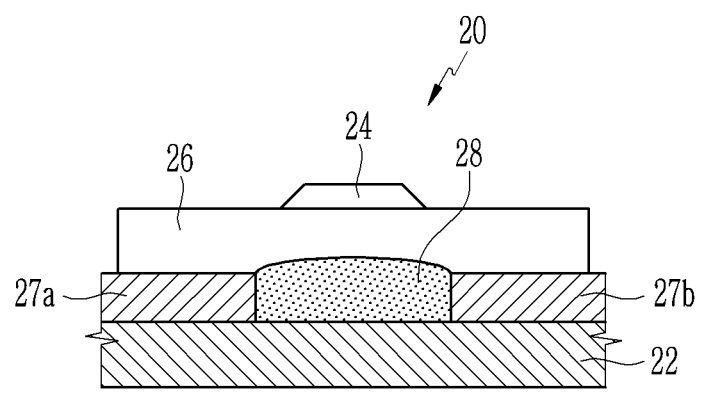
FIG. 2 is a schematic cross-sectional view of a transistor according to another embodiment.

FIGS. 1 and 2 are schematic cross-sectional views showing transistors according to example embodiments. The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or a metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but it is not limited thereto.

The insulation layers 16 and 26 may include a generally-used insulator having a higher dielectric constant, particularly, a ferroelectric insulator, e.g., $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator, e.g., $PbZr_{O.33}Ti_{O.66}O_3$ (PZT), $Bi_4Ti_3O_{12}$, $BaMgF_4$, $SrBi_2(TaNb)_2O_9$, $Ba(ZrTi)O_3$(BZT), $BaTiO_3$, $SrTiO_3$, $SiO_2$, $SiN_x$ (x is determined depending on the valence of Si), (aluminum oxynitride), etc.; or an organic insulator, e.g., polyimide, BCB (benzocyclobutane), parylene, polyacrylate, polyvinyl alcohol, polyvinylphenol, etc., but it is not limited thereto. Even though not mentioned above, an inorganic insulator described in U.S. Pat. No. 5,946,551, an organic insulator described in U.S. Pat. No. 6,232,157 and the like may be used as the insulation layers 16 and 26.

Hereinafter, the embodiments are illustrated in more detail with reference to examples. These examples, however, are not in any sense to be interpreted as limiting the scope of the present disclosure.

Synthesis of Fused Polycyclic Heteroaromatic Compound

Synthesis Example 1

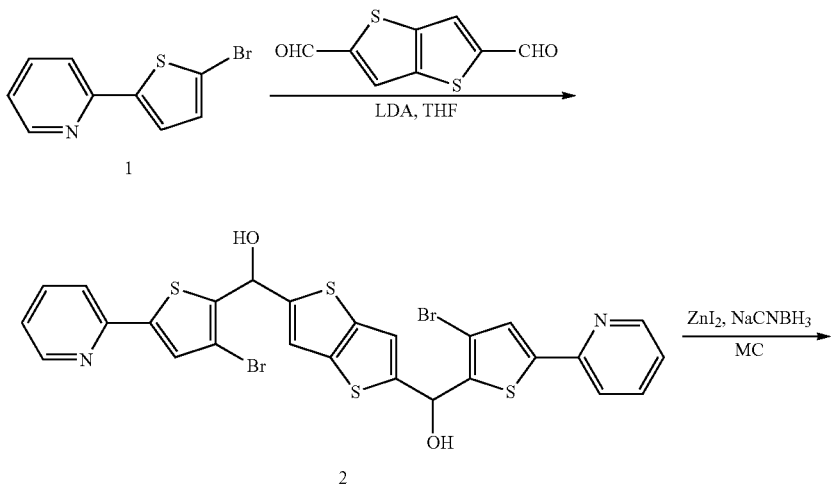

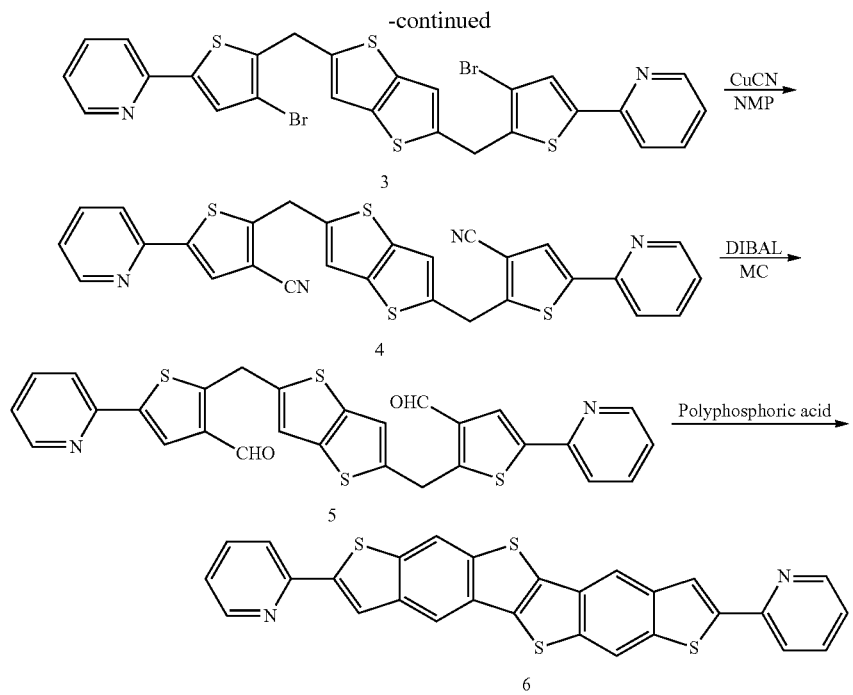

(1) Synthesis of Compound 2

Compound 1 (20.1 g, 83.8 mmol) is dissolved in 1.6 L of dry tetrahydrofuran (THF), the solution is slowly added in a dropwise fashion to LDA (a 2 M solution, 52.4 ml, 104.8 mmol) cooled down to −78° C., and the obtained mixture is stirred for 2 hours. Subsequently, thieno[3,2-b]thiophene-2,5-dicarbaldehyde (8.2 g, 41.9 mmol) is slowly added in a dropwise fashion to the solution which becomes opaque, and the obtained mixture is slowly heated up and stirred for 12 hours. 100 mL of a chloride-saturated aqueous solution is added thereto, and a THF layer therein is dried with $MgSO_4$. A precipitate produced by adding ethylacetate thereto is filtered to obtain Compound 1. (Yield: 86%).

1H-NMR (300 MHz, THF-$d_4$): δ 8.47 (d, J=4.2 Hz, 1H), 7.74 (m, 2H), 7.54 (s, 1H), 7.18 (m, 2H), 6.26 (d, J=3.6 Hz, 1H), 5.90 (d, J=3.6 Hz, 1H)

(2) Synthesis of Compound 3

Compound 2 (30 g, 44.4 mmol) is dissolved in 1.7 L of dichloroethane, and $ZnI_2$ (45.3 g, 141.9 mmol) and $NaCNBH_3$ (39.0 g, 620.9 mmol) are slowly added thereto. The mixture is stirred at 100° C. for 12 hours, and 500 mL of a 5% citric acid aqueous solution is added thereto. An organic layer is recovered from the mixed solution, washed with water, dried with $MgSO_4$, and concentrated under a reduced pressure to obtain Compound 3. (Yield: 90%)

1H-NMR (300 MHz, THF-$d_4$): δ 8.43 (d, J=4.2 Hz, 1H), 7.72 (m, 2H), 7.57 (s, 1H), 7.13 (m, 2H), 4.39 (s, 2H)

(3) Synthesis of Compound 4

Compound 3 (45 g, 69.8 mmol) is dissolved in 1.7 L of N-methylpyrrolidone, and copper cyanide (CuCN) (31 g, 349.1 mmol) is added thereto and reacted therewith under a Dean-Stark trap reflux condition (190° C.) for 12 hours. When the reaction is complete, the resultant is poured into a 1N HCl solution, and the mixture is stirred for 30 minutes. A solid produced therein is filtered and washed with acetonitrile and dried to obtain Compound 4. (Yield: 90%)

1H-NMR (300 MHz, THF-$d_4$): δ 8.44 (d, J=4.2 Hz, 1H), 7.78 (m, 3H), 7.24 (m, 2H), 4.62 (s, 2H)

(4) Synthesis of Compound 5

Compound 4 (10.4 g, 19.4 mmol) is dissolved in 1 L of dichloromethane, and a temperature of the solution is decreased down to 0° C. Diisobutyl aluminium hydride (DIBALH, a 1.0 M solution in cyclohexane, 44.6 ml, 44.6 mmol) is added thereto, and the obtained mixture is stirred for 5 minutes. The reaction solution is poured into a mixed solution of methanol and water (methanol:water=2:1) to complete a reaction, an organic layer is extracted with dichloromethane, washed with water and brine, dried with $MgSO_4$, and concentrated under a reduced pressure, and then, a component dissolved in chloroform therefrom is extracted and dried to obtain Compound 5. (Yield: 50%)

1H-NMR (300 MHz, $CDCl_3$): δ 10.09 (s, 1H), 8.52 (d, J=4.8 Hz, 1H), 7.83 (s, 1H), 7.69 (m, 2H), 7.18 (m, 1H), 7.08 (s, 1H), 4.78 (s, 2H)

(5) Synthesis of Compound 6

Polyphosphoric acid (200 g) is added to Compound 5 (5.6 g, 10.3 mmol), and the mixture is stirred at 90° C. for 6 hours. The resultant is cooled down to room temperature, 250 mL of water is added hereto, and a precipitate produced therein is settled down and recovered by using a centrifuge. This recovered material is sequentially washed with water, methanol, and dichloromethane in order to obtain Compound 6 as a yellow solid. (Yield: 50%).

MS (MALDI-TOF-MS, m/z) 505.935 (M+)

Figure 3:
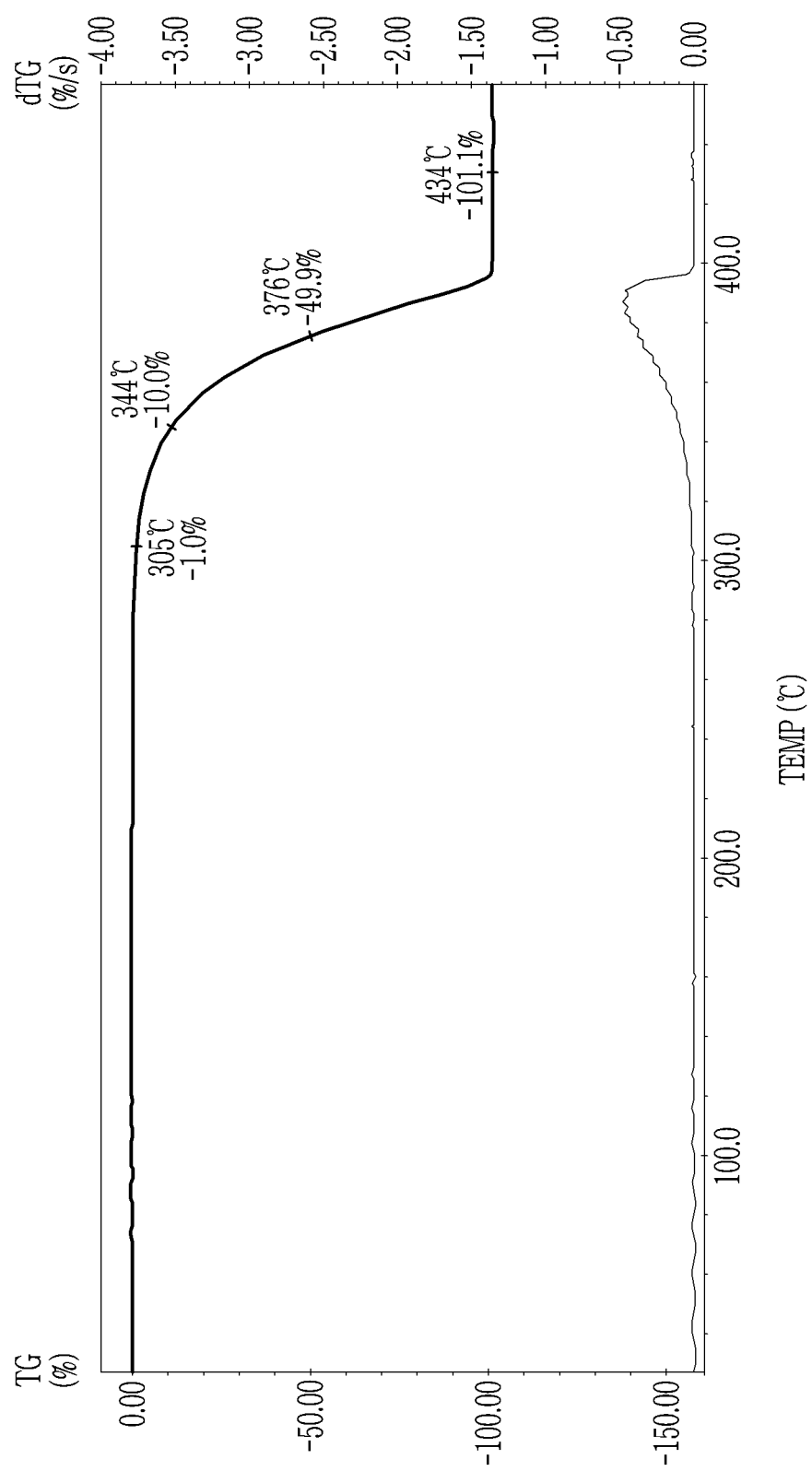
FIG. 3 is a graph showing thermogravimetric analysis (TGA) of the compound obtained according to Synthesis Example 1.

FIG. 3 shows a thermal gravimetric analysis (TGA) graph of Compound 6 according to Synthesis Example 1, and referring to FIG. 3, which confirms that Compound 6 according to Synthesis Example 1 is obtained well.

Synthesis Example 2

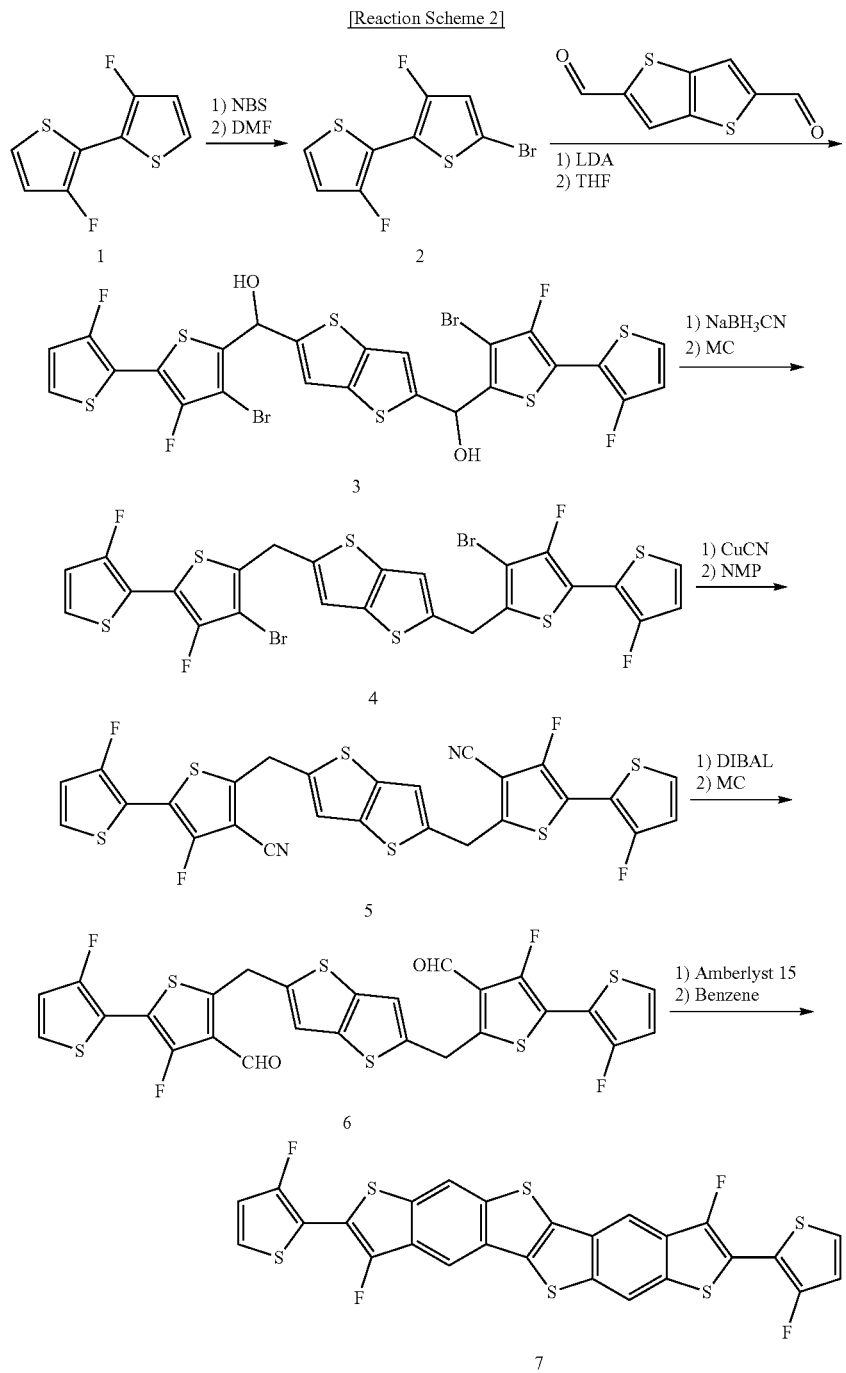

(1) Synthesis of Compound 2

Compound 1 (10 g, 49.4 mmol) is dissolved in 150 mL of dimethyl formamide (N,N-dimethylmethanamide) at 0° C., and N-bromo succinimide (8.7 g, 49.4 mmol) is added thereto in a dropwise fashion for a bromination. The mixture is reacted at room temperature for 12 hours, water is added thereto, and an extract is obtained by using dichloromethane. The extract is washed with water, dried with MgSO—4, concentrated under a reduced pressure, and then, purified through column chromatography using silica gel (and/or hexane) to obtain Compound 2. (Yield: 40%).

1H-NMR (300 MHz, CDCl$_3$): δ 7.179 (m, 1H), 6.88 (s, 1H), 6.84 (d, J=5.4 Hz, 1H)

(2) Synthesis of Compound 3

Compound 2 (8.0 g, 28.6 mmol) is dissolved in dry tetrahydrofuran (THF, 700 mL), the solution is cooled down to −78° C., LDA (a 2 M solution, 15 ml, 30.0 mmol) is slowly added thereto in a dropwise fashion, and the mixture is stirred at −78° C. for 2 hours. Subsequently, thieno[3,2-b]thiophene-2,5-dicarbaldehyde is added in a dropwise fashion to the solution which becomes opaque, and the mixture is slowly heated up to room temperature and stirred for 12 hours. 100 mL of a sodium bicarbonate-saturated aqueous solution is added thereto, and the obtained mixture is extracted with dichloromethane and washed with water. The resultant is dried with MgSO—$_4$ and concentrated under a reduced pressure and then, dissolved in 50 mL of a mixed solvent of EA/CHCl$_3$ (EA:CHCl$_3$=1:5), and a precipitate obtained by adding hexane thereto is filtered to obtain Compound 3 as yellow powder. (Yield: 81%).

1H-NMR (300 MHz, CDCl$_3$): δ 7.22 (m, 2H), 6.86 (d, J=5.7 Hz, 1H), 6.37 (s, 1H), 2.75 (s, 1H)

(3) Synthesis of Compound 4

Compound 3 (5.0 g, 6.6 mmol) is dissolved in 1 L of dichloromethane, and ZnI$_2$ (6.7 g, 21.1 mmol) and NaCNBH$_3$ (5.8 g, 92.4 mmol) are slowly added thereto. The mixture is stirred at room temperature for 2 hours, respectively washed with an ammonium chloride-saturated solution and water, dried with MgSO$_4$, and concentrated under a reduced pressure to obtain Compound 4. (Yield: 80%).

1H-NMR (300 MHz, CDCl$_3$): δ 7.19 (m, 1H), 7.05 (s, 1H), 6.83 (d, J=5.4 Hz, 1H), 4.32 (s, 2H)

(4) Synthesis of Compound 5

Compound 4 (1 g, 1.38 mmol) is dissolved in 15 ml of N-methylpyrrolidone, copper cyanide (CuCN) (0.5 g, 5.8 mmol) is added thereto, and the mixture is reacted in a microwave reactor under a condition of 50 W at 180° C. for 1.5 hours. When the reaction is complete, the resultant is poured into a 1N HCl solution, and the mixture is stirred for 30 minutes. After filtering a solid therein, an extract is obtained with dichloromethane and washed with water. The obtained product is dried with magnesium sulfate and purified/filtered with celite and silica to obtain Compound 5. (Yield: 54%)

1H-NMR (300 MHz, CDCl$_3$): δ 7.24 (m, 1H), 7.12 (s, 1H), 6.84 (d, J=5.4 Hz, 1H), 4.51 (s, 2H)

(5) Synthesis of Compound 6

Compound 5 (6.0 g, 9.7 mmol) is dissolved in 1 L of dichloromethane, and a temperature of the solution is decreased down to 0° C. Diisobutyl aluminum hydride (DIBALH, a 1.0 M solution in cyclohexane, 44.7 ml, 44.7 mmol) is added thereto, and the obtained mixture is stirred for 5 minutes. The reaction solution is poured into a mixed solution of methanol and water (methanol:water=2:1) to complete a reaction, an extract is obtained with dichloromethane and washed with water and brine, an organic layer therefrom is dried with MgSO$_4$ and concentrated under a reduced pressure and then, purified through silica chromatography to obtain Compound 6. (Yield: 21.5%)

1H-NMR (300 MHz, CDCl$_3$): δ 10.02 (s, 1H), 7.24 (m, 1H), 7.11 (s, 1H), 6.84 (d, J=5.4 Hz, 1H), 4.74 (s, 2H)

(6) Synthesis of Compound 7

Compound 6 (1.3 g, 2.1 mmol) is dissolved in 250 mL of benzene, Amberlyst 15 (6 g, Sigma-Aldrich Co., Ltd.) is added thereto, and water is removed therefrom, while the mixture is stirred and refluxed by using a Dean-Stark trap. After three days, the resultant is cooled down to room temperature, Amberlyst 15 (Sigma-Aldrich Co., Ltd.) is precipitated, and a yellow float is removed therefrom to obtain Compound 7. (Yield: 40%).

MS (MALDI-TOF-MS, m/z) 587.948 (M+)

Figure 4:
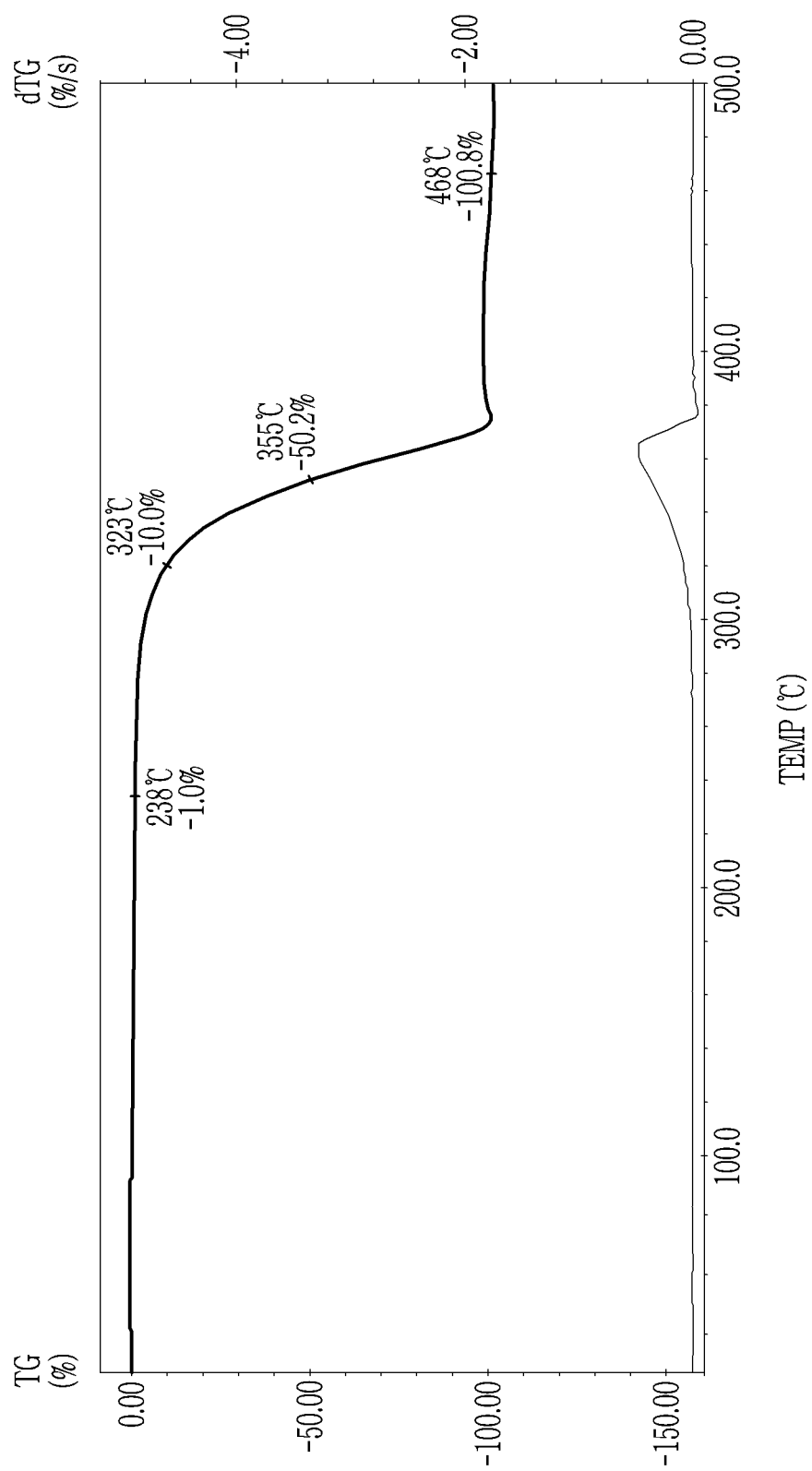
FIG. 4 is a graph showing thermogravimetric analysis (TGA) of the compound obtained according to Synthesis Example 2.

FIG. 4 is a thermogravimetric analysis (TGA) graph showing Compound 7 according to Synthesis Example 2, and referring to FIG. 4, Compound 7 according to Synthesis Example 2 is well obtained.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A fused polycyclic heteroaromatic compound represented by Chemical Formula 1:

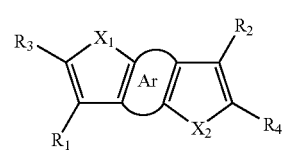

[Chemical Formula 1]

wherein, in Chemical Formula 1, $X_1$ and $X_2$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, Ar is a substituted or unsubstituted C6 to C30 aromatic ring, a substituted or unsubstituted C3 to C30 heteroaromatic ring, or a fused ring including the fused two or more rings, Ar is combined with an $X_1$-containing hetero ring and an $X_2$-containing hetero ring to provide a condensed polycyclic ring, $R_1$ and $R_2$ are independently hydrogen or a halogen atom, and $R_3$ and $R_4$ of Chemical Formula 1 are independently one of heterocyclic groups represented by Chemical Formula 2-1 and Chemical Formula 2-2:

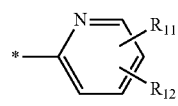

[Chemical Formula 2-1]

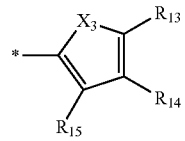

[Chemical Formula 2-2]

wherein, in Chemical Formula 2-1 and Chemical Formula 2-2, $X_3$ is S, Se, or Te, $R_{11}$ and $R_{12}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{11}$ and $R_{12}$ are independently present alone or combined to provide a ring, $R_{13}$ and $R_{14}$ are hydrogen or are a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, or a combination thereof combined to provide a ring, $R_{15}$ is a halogen atom, and \* is a linking point with the condensed polycyclic ring of Chemical Formula 1, and wherein the condensed polycyclic ring and the heterocyclic group represented by Chemical Formula 2-1 or Chemical Formula 2-2 are substantially present in the same plane.

2. The fused polycyclic heteroaromatic compound of claim 1, wherein $R_{11}$ to $R_{14}$ are independently hydrogen.

3. The fused polycyclic heteroaromatic compound of claim 1, wherein at least one of $R_1$ and $R_2$ is a halogen atom.

4. The fused polycyclic heteroaromatic compound of claim 1, wherein Ar has four to eight rings.

5. The fused polycyclic heteroaromatic compound of claim 1, wherein the condensed polycyclic ring is represented by one of Chemical Formula 3-1 to Chemical Formula 3-16:

(3-1)

(3-2)

(3-3)

(3-4)

(3-5)

(3-6)

(3-7)

(3-8)

-continued

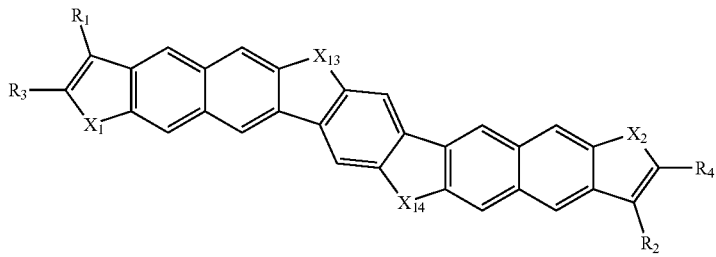
(3-9)

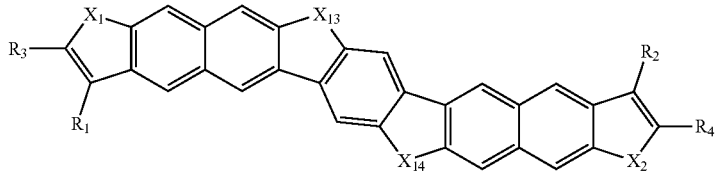
(3-10)

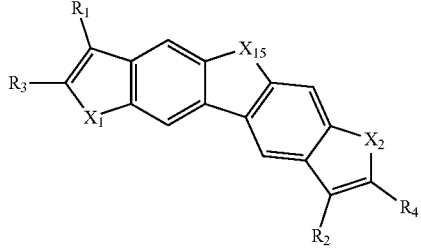
(3-11)

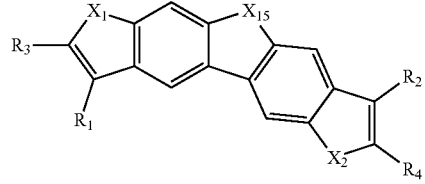
(3-12)

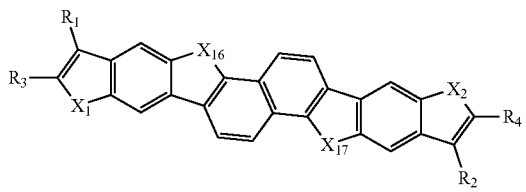
(3-13)

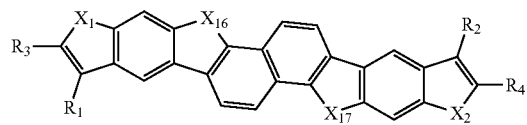
(3-14)

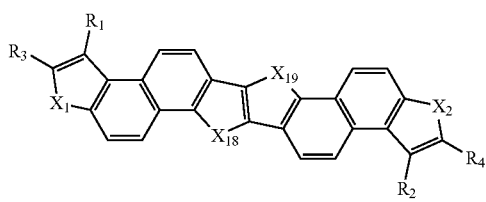
(3-15)

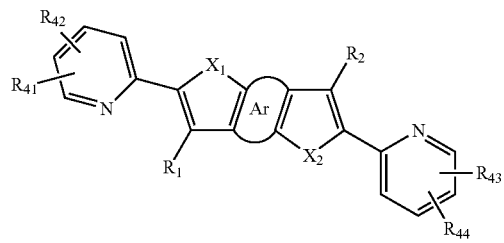
(3-16)

wherein, in Chemical Formula 3-1 to Chemical Formula 3-16, $X_1$, $X_2$, $R_1$, $R_2$, $R_3$, and $R_4$ are the same as in Chemical Formula 1, $X_{11}$ to $X_{19}$ are independently O, S, Se, Te, or N—$R^a$, wherein $R^a$ is hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof.

6. The fused polycyclic heteroaromatic compound of claim 1, wherein $R_3$ and $R_4$ have the same heterocyclic groups.

7. The fused polycyclic heteroaromatic compound of claim 1, wherein the fused polycyclic heteroaromatic compound is represented by Chemical Formula 4:

[Chemical Formula 4]

wherein, in Chemical Formula 4, $X_1$, $X_2$, Ar, $R_1$, and $R_2$ are the same as in Chemical Formula 1, $R_{41}$ to $R_{44}$ are independently hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, $R_{41}$ and $R_{42}$ are independently present alone or adjacent two thereof are combined to provide a ring, and $R_{43}$ and $R_{44}$ are independently present alone or adjacent two thereof are combined to provide a ring.

8. The fused polycyclic heteroaromatic compound of claim 7, wherein the fused polycyclic heteroaromatic compound is represented by one of Chemical Formula 5-1 to Chemical Formula 5-36:

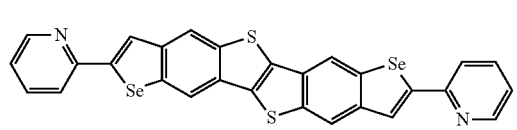

(5-1)

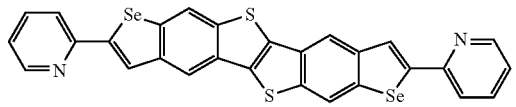

(5-2)

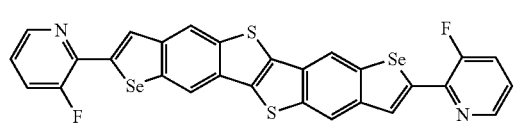

(5-3)

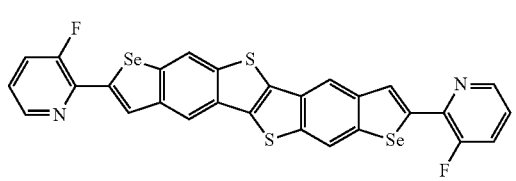

(5-4)

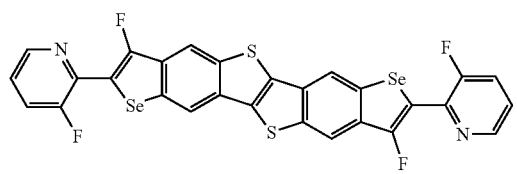

(5-5)

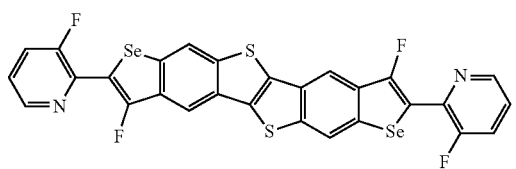

(5-6)

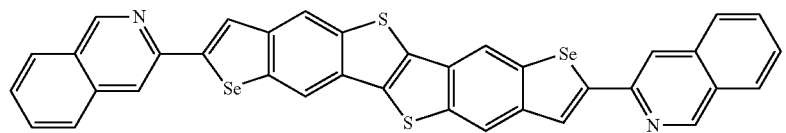

(5-7)

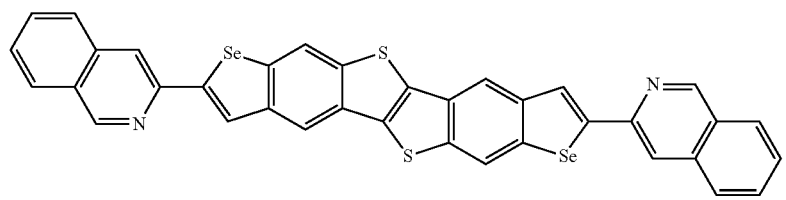

(5-8)

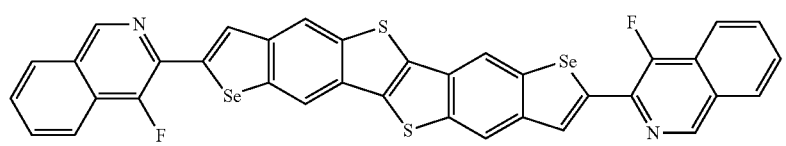

(5-9)

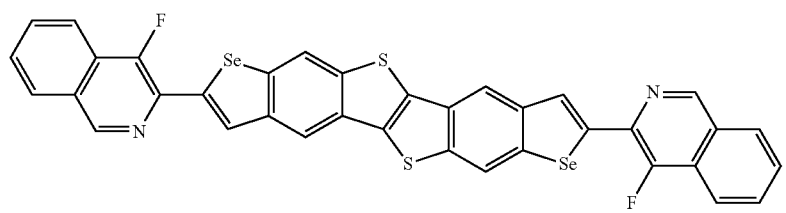

(5-10)

-continued
(5-11)
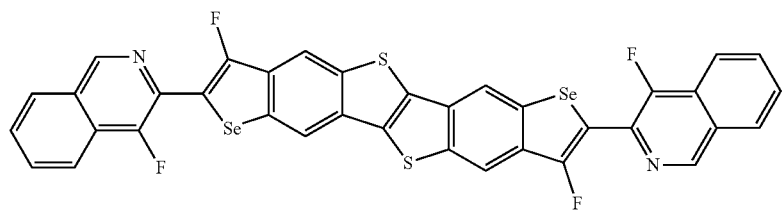
(5-12)
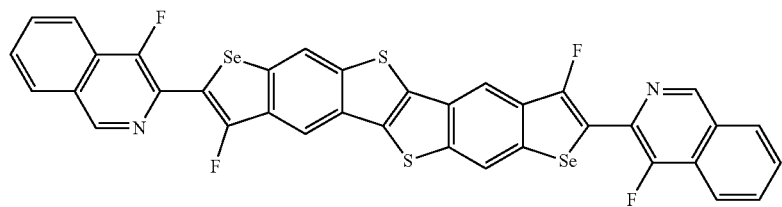
(5-13)
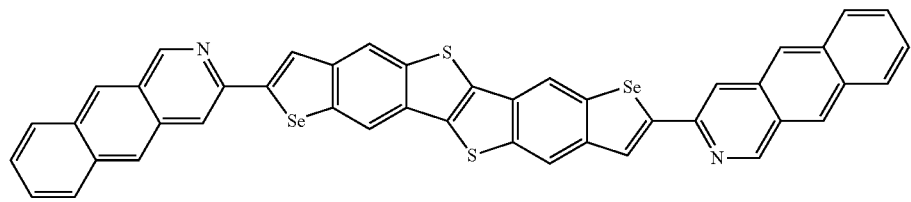
(5-14)
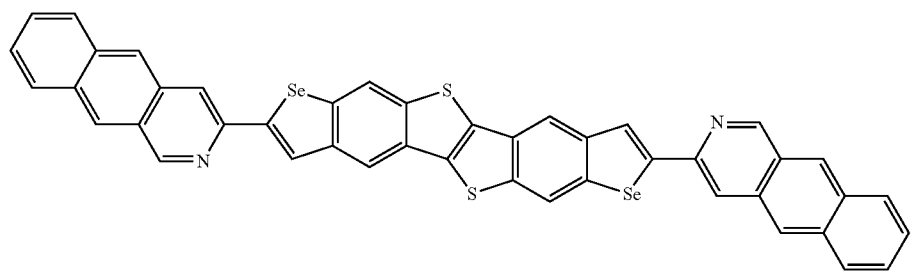
(5-15)
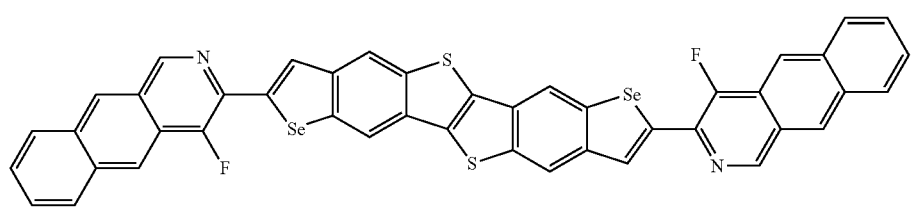
(5-16)
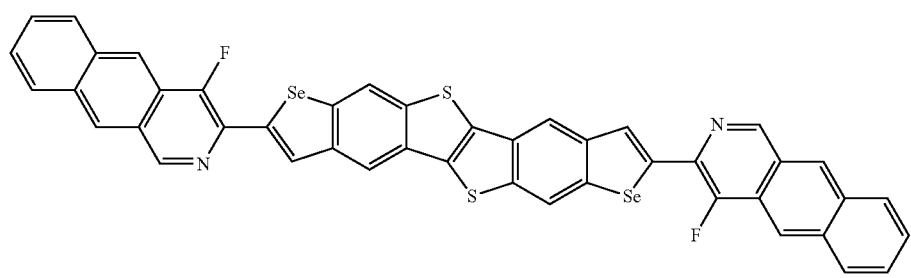
(5-17)
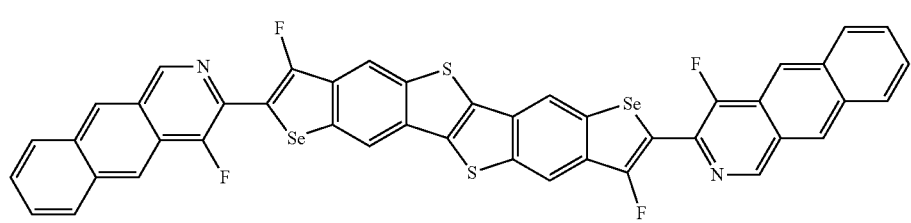

-continued
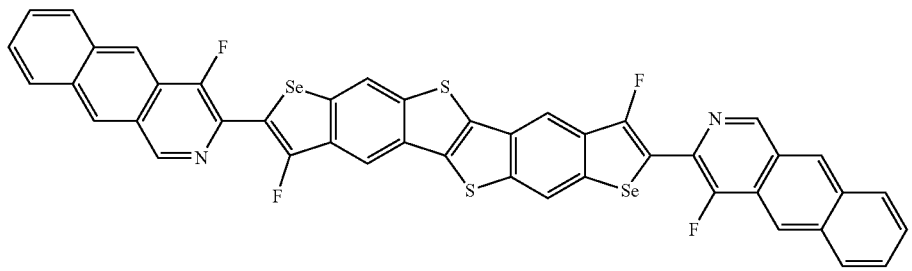
(5-18)
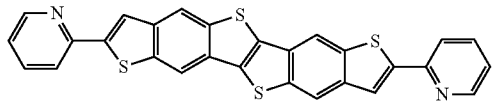
(5-19)
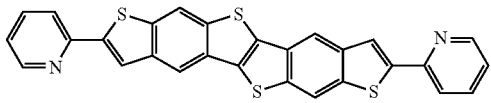
(5-20)
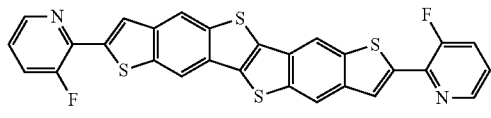
(5-21)
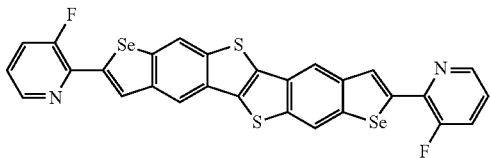
(5-22)
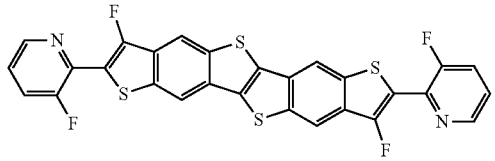
(5-23)
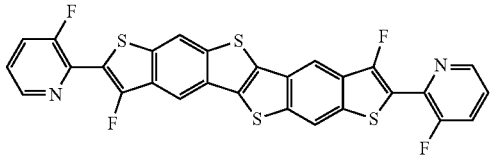
(5-24)
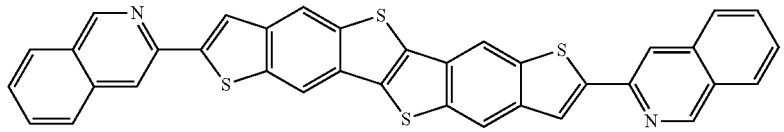
(5-25)
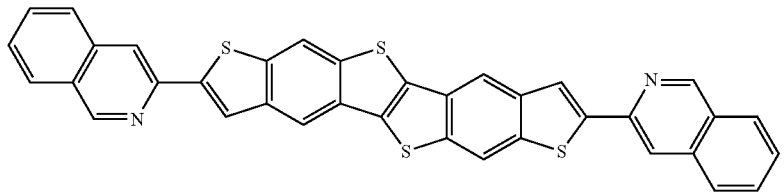
(5-26)
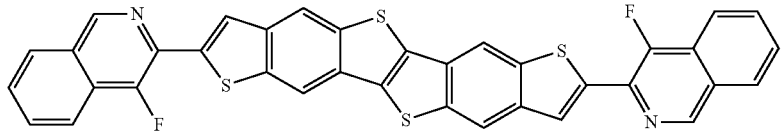
(5-27)
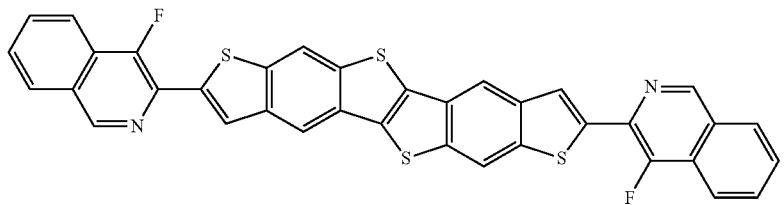
(5-28)

-continued
(5-29)
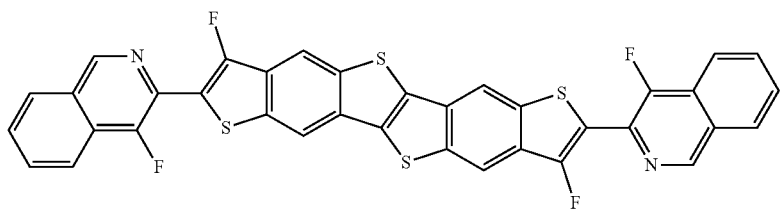
(5-30)
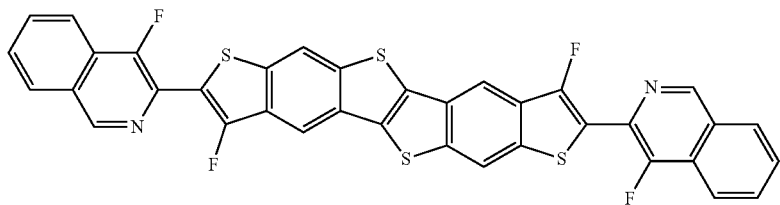
(5-31)
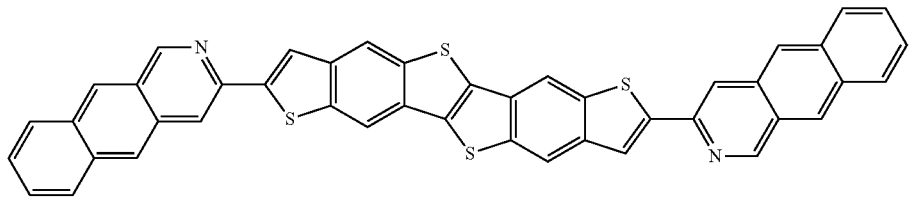
(5-32)
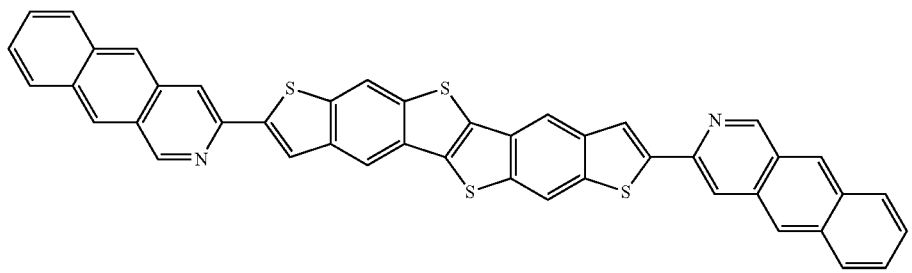
(5-33)
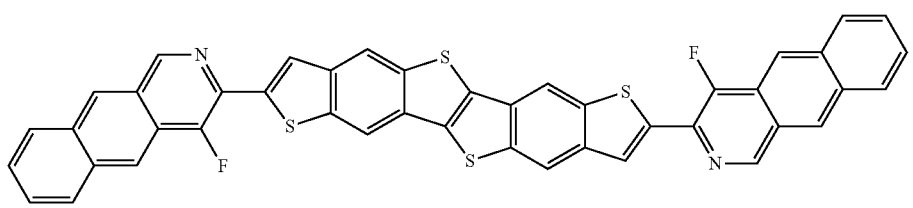
(5-34)
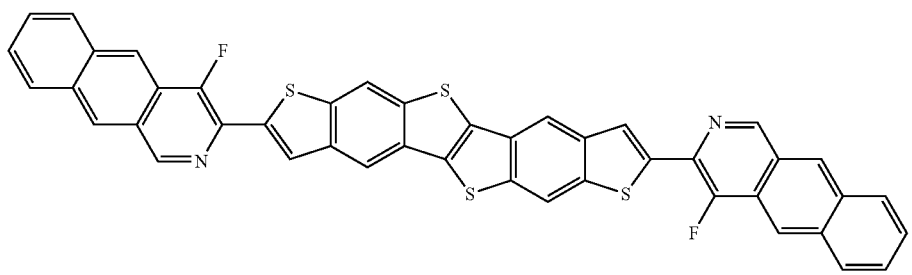
(5-35)
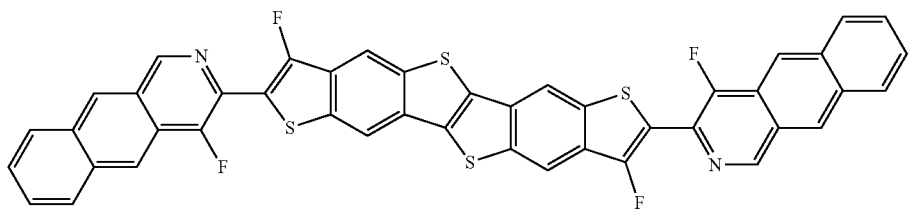

(5-36)

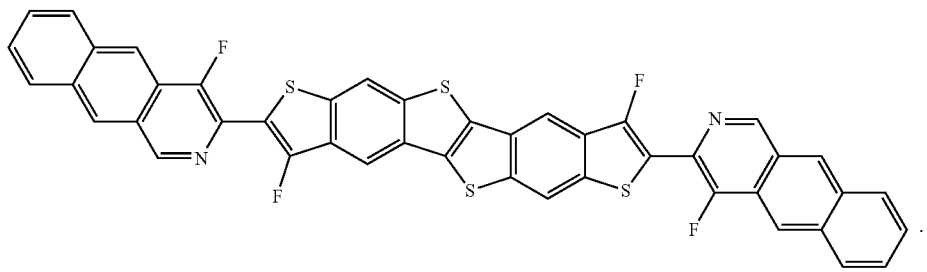

9. The fused polycyclic heteroaromatic compound of claim 1, wherein the fused polycyclic heteroaromatic compound is represented by Chemical Formula 6:

[Chemical Formula 6]

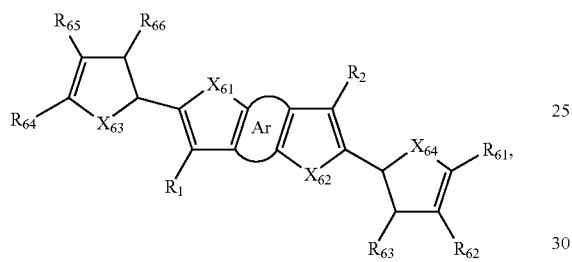

wherein, in Chemical Formula 6,
Ar, $R_1$, and $R_2$ are the same as in Chemical Formula 1,
$X_{61}$ to $X_{64}$ are independently S or Se,
$R_{63}$ and $R_{66}$ are independently a halogen atom,
$R_{61}$ and $R_{62}$ are hydrogen or a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, or a combination thereof combined to provide a ring, and $R_{64}$ and $R_{65}$ are hydrogen or a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, or a combination thereof combined to provide a ring.

10. The fused polycyclic heteroaromatic compound of claim 9, wherein the fused polycyclic heteroaromatic compound is represented by one of Chemical Formula 8-1 Chemical Formula 8-2, Chemical Formula 8-5 to Chemical Formula 8-6, and Chemical Formula 8-9 to Chemical Formula 8-16:

(8-1)

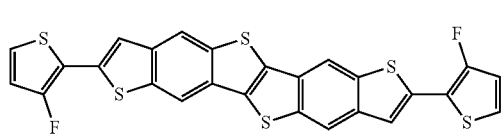

(8-2)

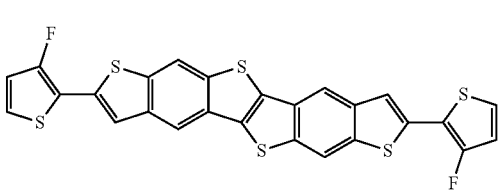

(8-3)

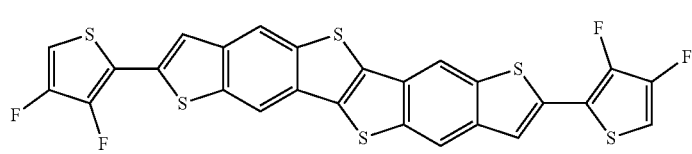

(8-4)

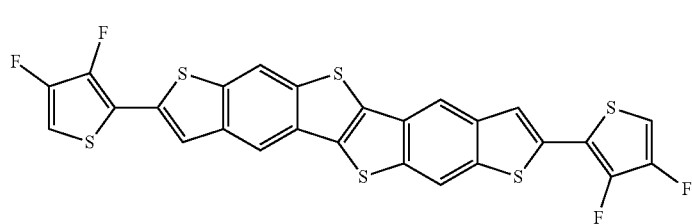

-continued
(8-5)
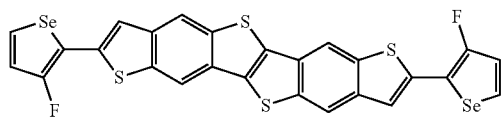
(8-6)
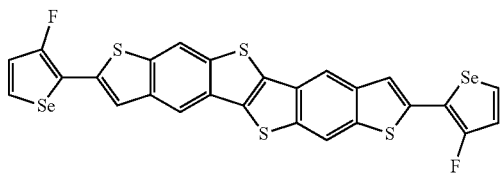
(8-7)
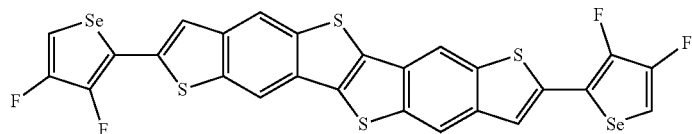
(8-8)
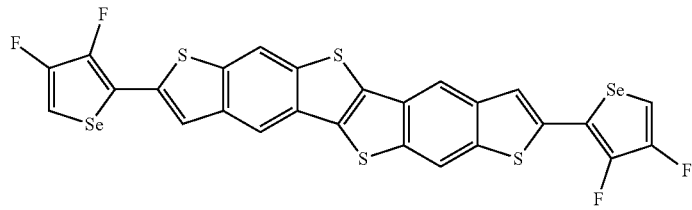
(8-9)
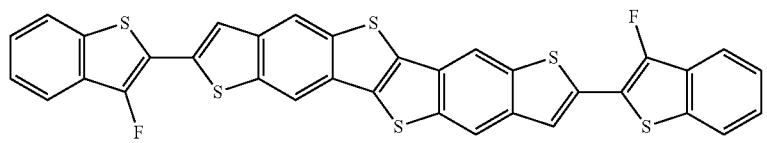
(8-10)
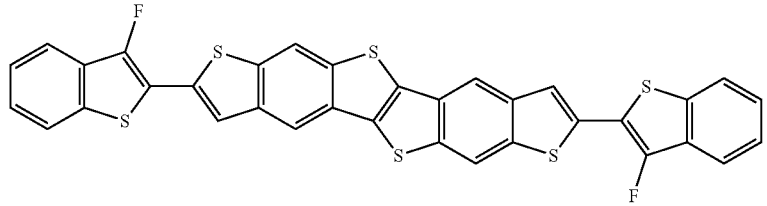
(8-11)
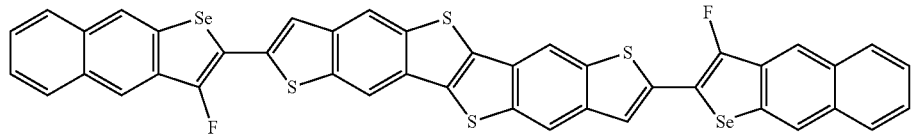
(8-12)
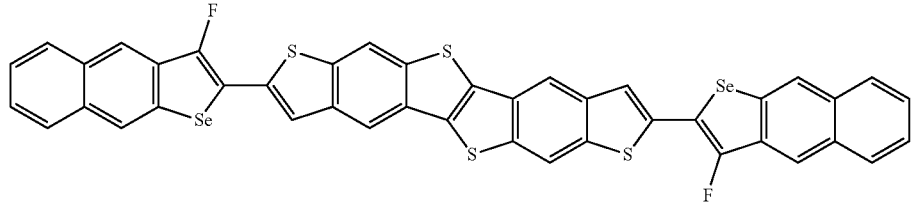
(8-13)
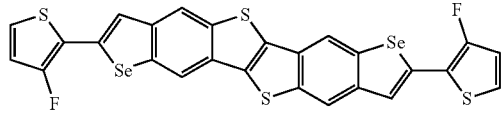
(8-14)
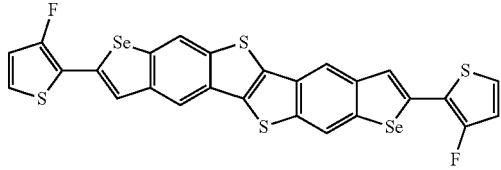
(8-15)
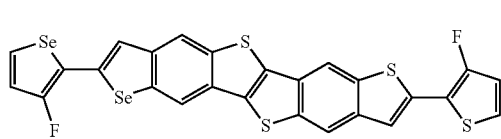
(8-16)
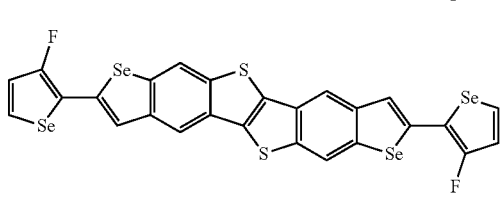

(8-17)
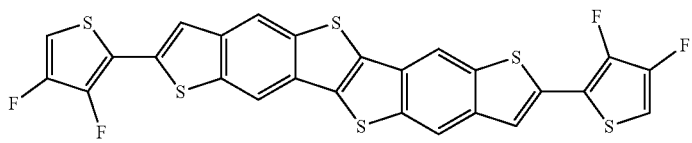
(8-18)
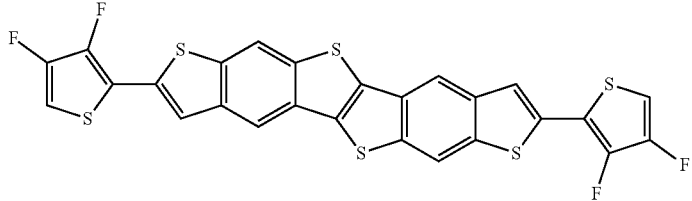
(8-19)
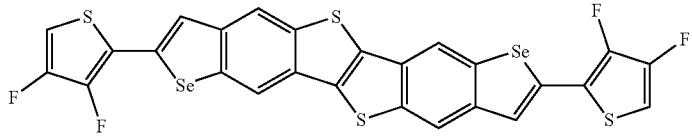
(8-20)
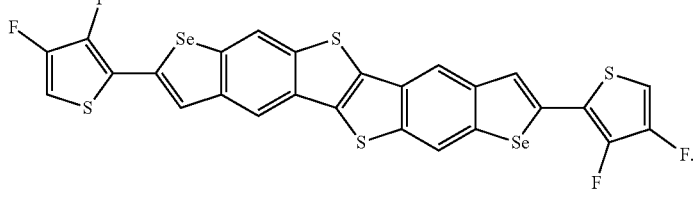
11. The fused polycyclic heteroaromatic compound of claim 9, wherein the fused polycyclic heteroaromatic compound is represented by one of Chemical Formula 9-1 to Chemical Formula 9-42:
(9-1)
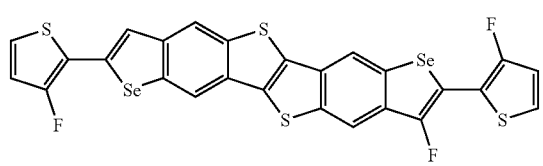
(9-2)
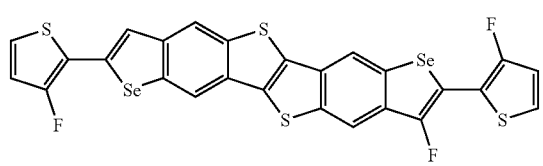
(9-3)
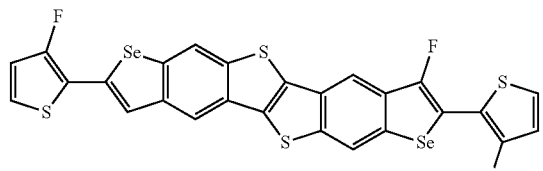
-continued
(9-4)
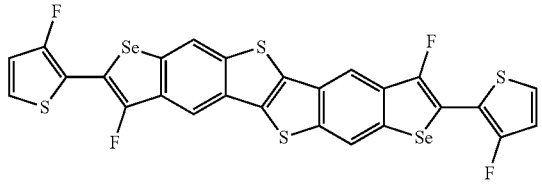
(9-5)
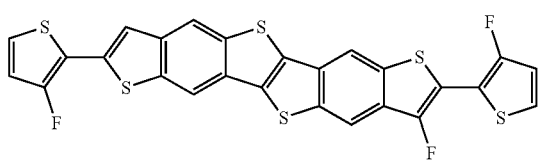
(9-6)
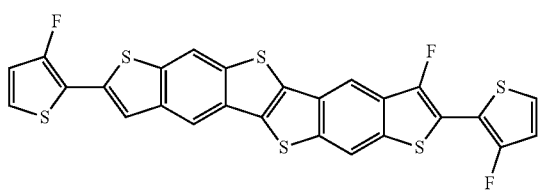
(9-7)
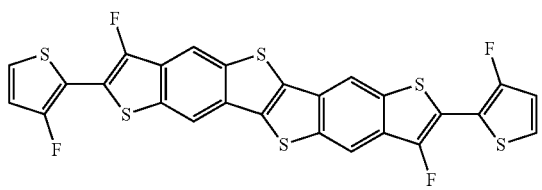
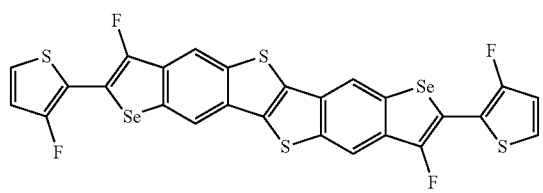

-continued
(9-8)
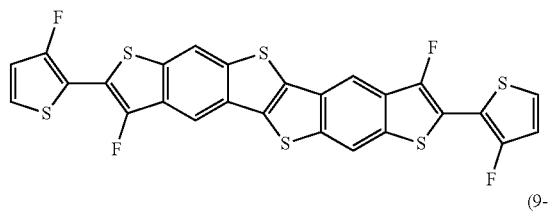
(9-9)
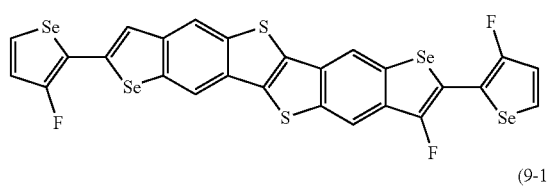
(9-10)
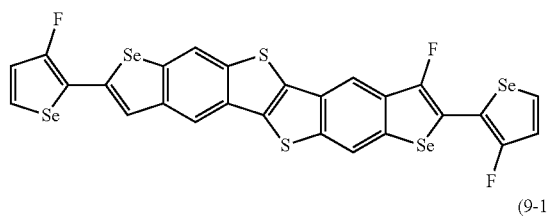
(9-11)
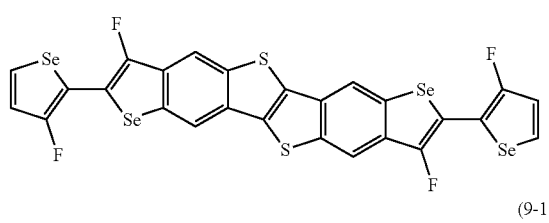
(9-12)
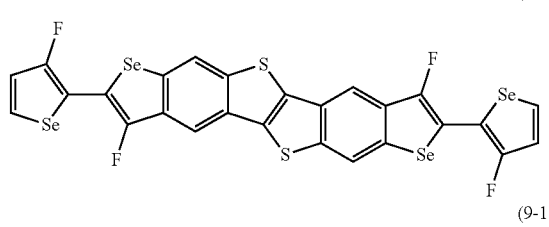
(9-13)
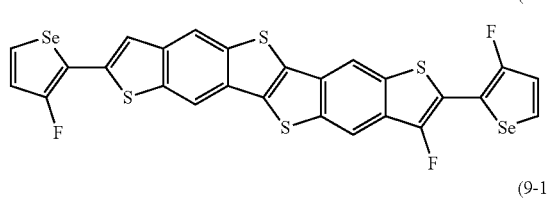
(9-14)
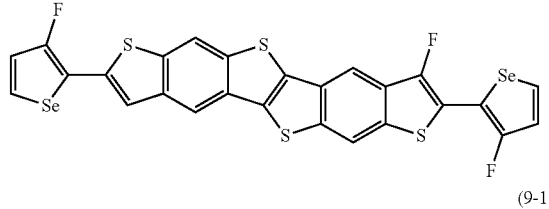
(9-15)
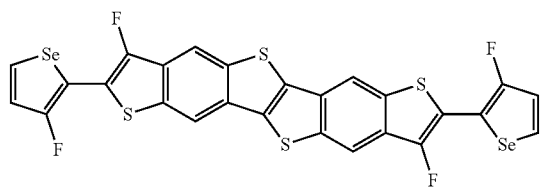
-continued
(9-16)
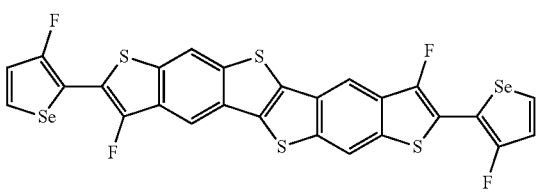
(9-17)
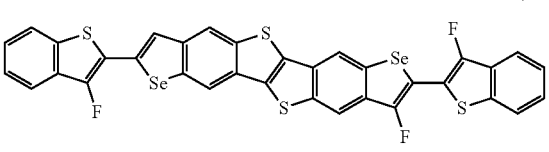
(9-18)
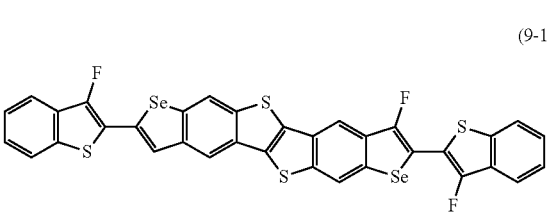
(9-19)
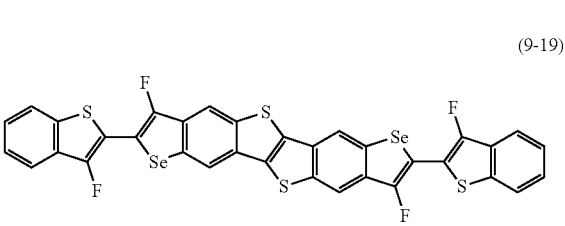
(9-20)
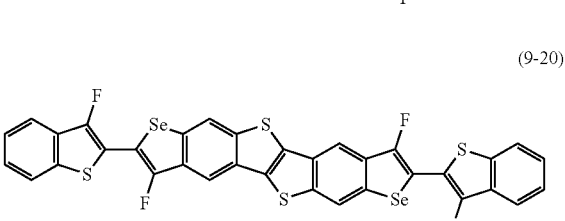
(9-21)
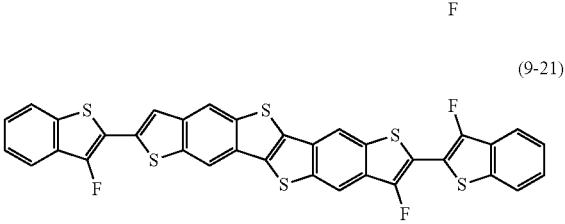
(9-22)
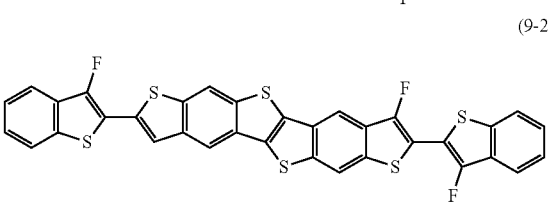
(9-23)
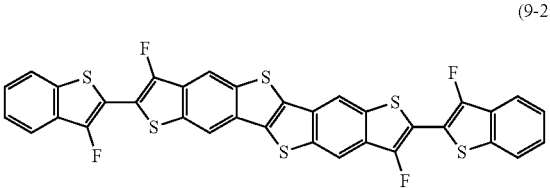

-continued
(9-24)
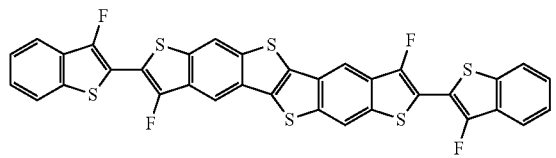
(9-25)
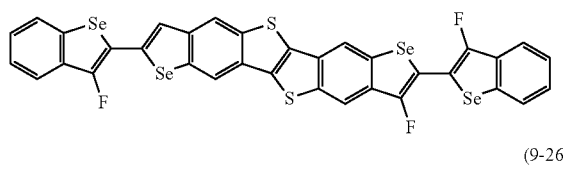
(9-26)
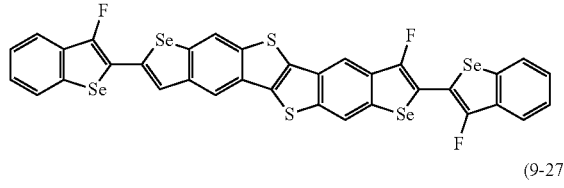
(9-27)
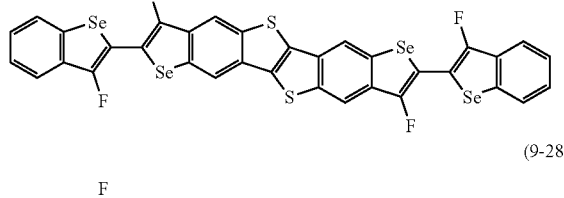
(9-28)
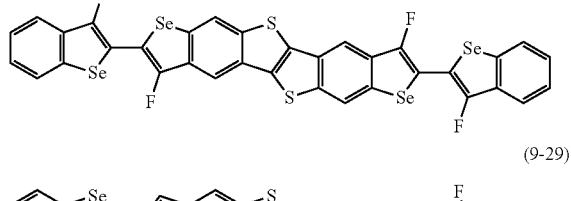
(9-29)
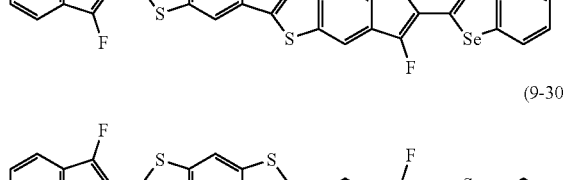
(9-30)
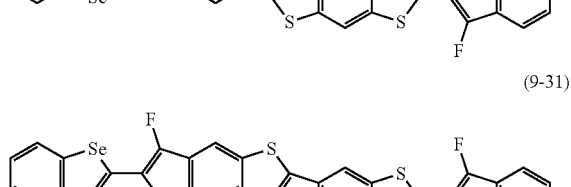
(9-31)
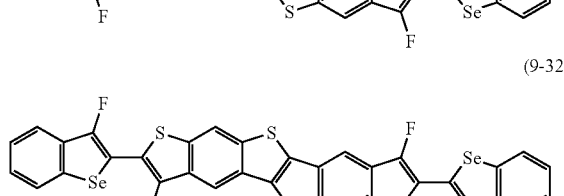
-continued
(9-33)
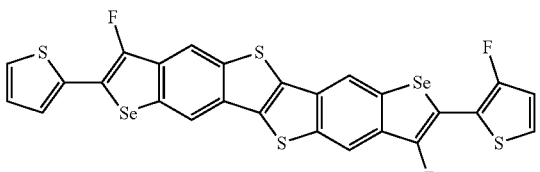
(9-34)
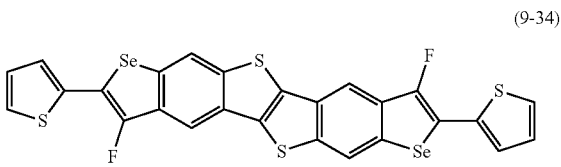
(9-35)
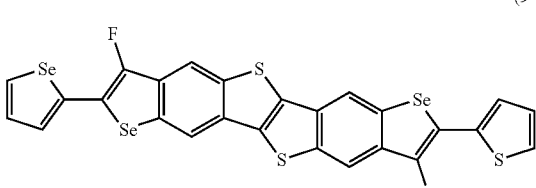
(9-36)
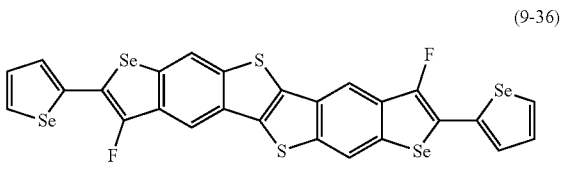
(9-37)
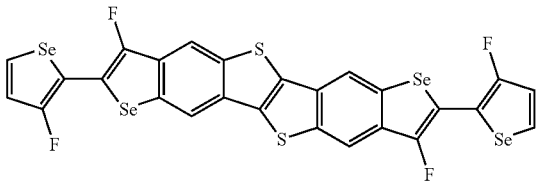
(9-38)
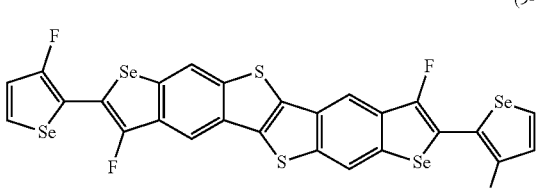
(9-39)
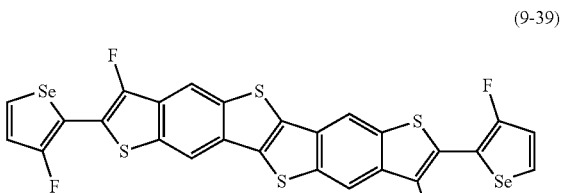
(9-40)
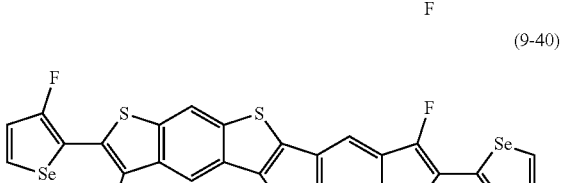
(9-32)

-continued

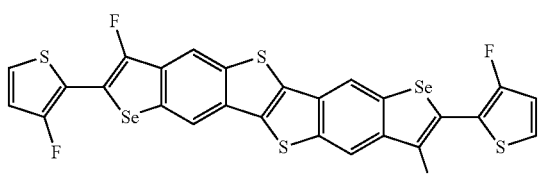
(9-41)

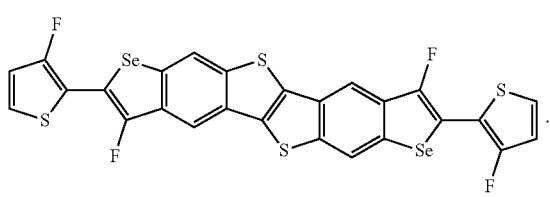
(9-42)

12. An organic thin film comprising the fused polycyclic heteroaromatic compound of claim 1.

13. A thin film transistor comprising
a gate electrode,
a semiconductor overlapping with the gate electrode, and
a source electrode and a drain electrode electrically connected to the semiconductor,
wherein the semiconductor includes the fused polycyclic heteroaromatic compound of claim 1.

14. An electronic device comprising the thin film transistor of claim 13.

15. The electronic device of claim 14, wherein the electronic device includes a solar cell, a liquid crystal display (LCD), an organic light emitting diode device, an eletrophoretic device, an organic photoelectric device, and organic sensor.

16. An electronic device comprising the organic thin film of claim 12.

* * * * *